US006780618B2

(12) United States Patent
Lee et al.

(10) Patent No.: US 6,780,618 B2
(45) Date of Patent: Aug. 24, 2004

(54) METHOD FOR IMPROVING GENETIC STABILITY OF FOREIGN INSERT NUCLEOTIDE SEQUENCE IN RECOMBINANT POLIOVIRUS

(75) Inventors: Sang-Gu Lee, Daejon Metropolitan (KR); Dae-You Kim, Daejon Metropolitan (KR); Ki-Tae Kim, Daejon Metropolitan (KR); Yong-Soo Bae, Daejon Metropolitan (KR)

(73) Assignee: CreaGene Inc. (KR)

( * ) Notice: Subject to any disclaimer, the term of this patent is extended or adjusted under 35 U.S.C. 154(b) by 0 days.

(21) Appl. No.: 10/071,867

(22) Filed: Feb. 8, 2002

(65) Prior Publication Data

US 2003/0166267 A1 Sep. 4, 2003

(30) Foreign Application Priority Data

Feb. 8, 2001 (KR) .......................................... 2001-6229

(51) Int. Cl.[7] ......................... C12N 15/68; C12N 15/86; C12N 7/01
(52) U.S. Cl. ................ 435/91.4; 435/91.41; 435/235.1; 435/320.1; 435/440; 435/456; 435/471; 435/472; 435/475
(58) Field of Search ............................. 435/91.4, 91.41, 435/320.1, 235.1, 440, 456, 471, 472, 475; 424/199.1

(56) References Cited

U.S. PATENT DOCUMENTS 6,060,308 A * 5/2000 Parrington ................ 435/320.1

FOREIGN PATENT DOCUMENTS

WO 02/042326 * 11/2000 ........... C07K/14/08

OTHER PUBLICATIONS

Strauss et al. Fields Virology, third edition, ed. B.N. Fields, pp. 153–171, Raven publishers, Philadelphia, 1996.*

Rima et al (Journal of General Virology 78:2859–2870, 1997).*

Jenkins et al (Journal of Molecular Evolution 52:383–390, 2001).*

Lee et al (Journal of Virology 76(4):1649–1662, 2002).*

Tang et al, "Toward a Poliovirus–Based Simian Immunodeficiency Virus Vaccine: Correlation between Genetic Stability and Immunogenicity", Journal of Virology, vol. 71, No. 10, Oct. 1997, pp. 7841–7850.

Mueller et al, "Expression of Foreign Proteins by Poliovirus Polyprotein Fusion: Analysis of Genetic Stability Reveals Rapid Deletions and Formation of Cardioviruslike Open Reading Frames", Journal of Virology, vol. 72, No. 1, Jan. 1998, pp. 20–31.

* cited by examiner

Primary Examiner—Mary E. Mosher
(74) Attorney, Agent, or Firm—Harness, Dickey & Pierce, P.L.C.

(57) ABSTRACT

The present invention relates to (a) methods for improving a genetic stability of an insert nucleotide sequence in a recombinant single-stranded RNA virus vector, which comprises performing a mutagenesis of the foreign insert nucleotide sequence to provide even distribution of G/C content throughout the overall foreign insert nucleotide sequence and/or to increase G/C content of the foreign insert without substantially causing amino acids substitutions (b) a recombinant single-stranded RNA virus comprising an insert nucleotide sequence with improved genetic stability and (c) a recombinant poliovirus comprising an insert nucleotide sequence with improved genetic stability.

45 Claims, 14 Drawing Sheets

Fig. 1

```
    735                                            771
5'-- GTATCATA ATG GGT GCT CAG GTT TCA TCA CAG AAA GT---3'
              M   G   A   Q   V   S   S   Q   K
```

```
          SstII        HpaI        EagI                        3C
      CCC CGG GTT AAC CGG CCG GCT TTG TTC CAA
       P   R   V   N   R   P   A   L   F   Q
```

Poliovirus Sabin 1
vector (RPS-Vax) system

*Group I*

PV 2-127 (●)   SIV p27-150 (●)

*Group II*

SIV env-108 (◉)   PV 2.3-131 (○)

*Group III*

HIV-1 mV3 (□*‡)   SIV p27-167 (□†)

SIV p27-150 (Group I)   SIV p27-167 (Group III)

Fig. 5a

SIV env-108 (G/C content, 35.4 %)

```
ACTTCTACTT GGTTTGGCTT TAATGGAACT AGAGCAGAAA ATAGAACTTA TATTTACTGG
    AGC       C        C C                G       G  C           C C

CATGGTAGGG ATAATAGGAC TATAATTAGT TTAAATAAGT ATTATAATCT AACAATGAAA
           C  CC      G  C   C  C CG    C             C  C  C  C  C

TGTAGAAGAC CAGGAAATAA GACAGTTTTA CCAGTCACCA TTATGTCTGG ATTGGTTTTC
  C  G                          GC            C    C  G         C

CACTCACAAC CAATCAATGA TAGGCCAAAG CAGGCATGGT GTTGGTTTGG AGGAAAATGG
   G     C      C         C         C               C        C  G

AAGGATGCAA TAAAAGAGGT GAAGCAGACC ATTGTCAAAC ATCCCAGGTA TACTGGAACT
       C          G                    G                C

AACAATACTG ATAAAATCAA TTTG
     C        C    G  -    SIV env-108/M (G/C content, 50.3%)
```

Fig. 5b

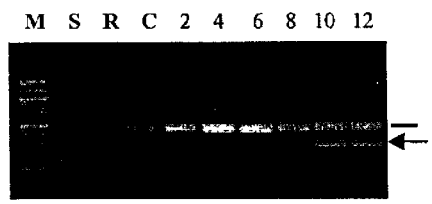

SIV env-108 (35.4%)

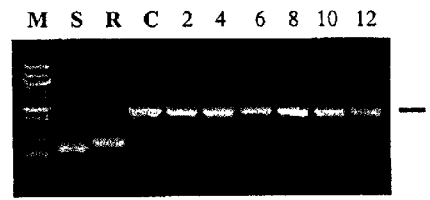

SIV env-108/ M (50.3%)

Fig. 5c

SIV gag-100 (G/C content, 45%)

```
AGCCCGAGAA CATTAAATGC CTGGGTAAAA TTGATAGAGG AAAAGAAATT TGGAGCAGAA
   T  A                A              A          A          A

GTAGTGCCAG GATTTCAGGC ACTGTCAGAA GGTTGCACCC CCTATGACAT TAATCAGATG
       T             A    T A         T T  A      T            A

TTAAATTGTG TGGGAGACCA TCAAGCGGCT ATGCAGATTA TCAGAGATAT TATAAACGAG
        A       T         A          A       A                T A

GAGGCTGCAG ATTGGGACTT GCAGCACCCA CAACCAGCTC CACAACAAGG ACAACTTAGG
    A               T  A  A  T                                T  A A

GAGCCGTCAG GATCAGATAT TGCAGGAACA ACTAGTTCAG TAGATGAACA AATCCAGTGG
     A  T                                                    T  A
```

- SIV gag-100/M (G/C content, 34%)

Fig. 5d

 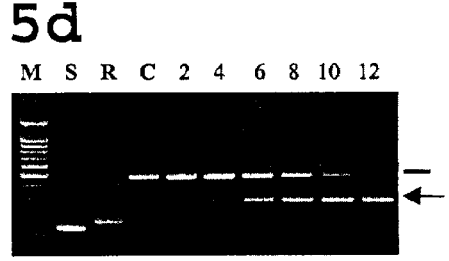

SIV gag-100 (45%)    SIV gag-100/M (34%)

Sequence-adjusted full-length synthetic insert

Fig. 9

```
1     A   K   A   V   A   A   W   T   L   K   A   A   A   G   Q   A   S   T   E   G   D   C   G   C   P    25
1     GCT AAG GCC GTT GCA GCC TGG ACC CTG AAA GCC GCT GCA GGC CAA GCC TCC ACC GAA GGC GAC TGC GGT TGC CCA  75

26    A   I   I   E   V   D   N   D   A   P   T   K   R   A   S   K   L   F   S   E   F   E   V   D   N    50
76    GCC ATT ATT GAA GTG GAT AAT GAT GCT CCA ACA AAG CGT GCC AGT AAA TTA TTC AGC GAA TTC GAG GTC GAT AAT 150
          C   C   G   C       C       C   T   C       A       C   G   C   C

51    E   Q   P   T   T   R   A   Q   K   L   F   A   M   W   R   I   T   Y   K   D   N   D   A   P   T    75
151   GAA CAA CCA ACC ACC CGG GCA CAG AAA CTC TTC GCC ATG TGG CGT ATC ACT TAC AAG GAT AAT GAT GCT CCA ACA 225
          G   G   C   T       A   C       G                                           C           G       T

76    K   R   A   S   K   L   C   V   R   I   Y   M   K   P   K   H   V   R   C   S   G   C   P   A   I   100
226   AAG CGT GCC AGT AAA TTA TGC GTC CGA ATC TAC ATG AAG CCC AAG CAC GTT CGA TGC TCC GGC TGT CCC GCC ATT 300
              C   A TC       C G                                                                       T

101   I   E   V   D   N   D   A   P   T   K   R   A   S   K   L   D   N   Y   Q   S   P   C   A   I   N   125
301   ATT GAA GTG GAT AAT GAT GCT CCA ACA AAG CGT GCC AGT AAA TTA GAC AAC TAC CAG TCC CCA TGC GCG ATC AAT 375
          C               C   C   A       C       A G    A TCA    G C G                                C

126   E   Q   P   T   T   R   A   Q   K   S   A   G   C   F   Y   Q   T   R   V   V   P   S   G   C       150
376   GAA CAA CCA ACC ACC CGG GCA CAG AAA TCC GCT GGG TGC TTC TAT CAG ACC CGC GTC GTG CTT CCC TCA GGT TGT 450
          G       T               T   G   A   G
```

Fig. 10

```
primer 1 ⟶
5-ATTATA CCGCGG
        (Sst II)
        10         20         30         40         50         60
     GCTAAGGCCG TTGCAGCCTG GACCCTGAAA GCCGCTGCAG GCCAAGCCTC CACCGAAGGC
                                                             3'-GTGGCTTCCG primer 3 ⟶
        70         80         90        100        110        120
     GACTG-3'                                 5'-ACCAA GCGAGCCAGC
     CTGACGCCAA CGGGTCGGTA GTAGCTCCAG CTATTGCTAC GGGGATGGTT CGCTCGGTCG-5'
                                                          ⟵ primer 2

130        140        150        160        170        180
     AAGCTCTTCA GCGAATTCGA GGTCGATAAT GAGCAGCCCA CTACCCGAGC CCAGA-3'
                                                 3'-GATGGGCTCG GGTCTTCGAG primer 5 ⟶
       190        200        210        220        230        240
                                    5'-TGCGC CAACTAAGCG CGCATCTAAA
     AAGCGGTACA CCGCATAGTG AATGTTCCTG TTACTACGCG GTTGATTCGC-5'
                                                 ⟵ primer 4

250        260        270        280        290        300
     CTGTGCGTCC GAATCTACAT GAAGCCCAAG CACGTTCGAT GCTCC-3'
                                       3'-GTGCAAGCTA CGAGGCCGAC AGGGCGATAA primer 7 ⟶
       310        320        330        340        350        360
                       5'-CCAAA CGGGCATCAA AGCTGGACAA CTACCAGTCC
     TAGCTTCACC TATTGCTGCG TGGTTGGTTT GCCCGTAGTT-5'
                                      ⟵ primer 6

370        380        390        400        410        420
     CCATGCGCGA TCAACGAGCA ACCTACCACC CGTGC-3'
                           3'-TGGATGGTGG GCACGCGTTT TCAGGCGACC CACGAAGATA 430        440        450
     GTCTGGGCGC AGCACCAAGG GAGTCCAACA-GCCGGC AATTAT-5'
                                           ⟵ (Eag I) primer 8
```

Fig. 13
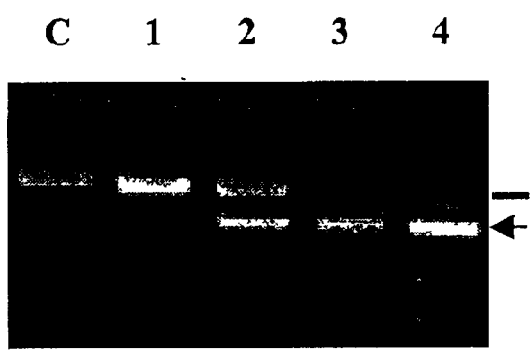
*PVm-150*
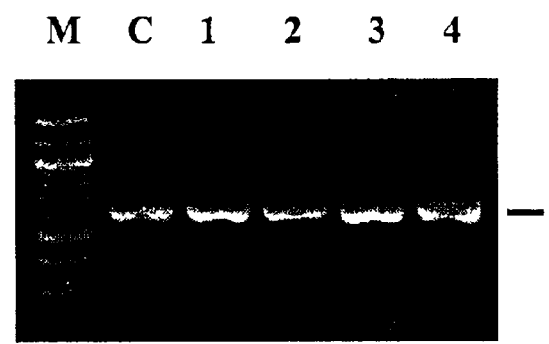
*PVm-150/M*

METHOD FOR IMPROVING GENETIC STABILITY OF FOREIGN INSERT NUCLEOTIDE SEQUENCE IN RECOMBINANT POLIOVIRUS

BACKGROUND OF THE INVENTION

1. Field of the Invention

The present invention relates to methods for improving a genetic stability of a foreign insert nucleotide sequence in a recombinant RNA virus and recombinant RNA viruses comprising a foreign insert nucleotide sequence with improved genetic stability. More particularly, the present invention relates to (a) methods for improving a genetic stability of a foreign insert nucleotide sequence in a recombinant RNA virus, (b) a recombinant single-stranded RNA virus comprising a foreign insert nucleotide sequence with improved genetic stability, (c) a recombinant poliovirus comprising a foreign insert nucleotide sequence with improved genetic stability, (d) methods for construction of sequence-adjusted exogeneous nucleotide or artificially synthesized foreign inserts nucleotide by template/ligation-free PCR, and (e) a vaccine composition comprising a recombinant single-stranded RNA virus.

2. Description of the Related Art

Live attenuated viral vaccines have been reported to have several advantages over other types of vaccines: low cost for production, higher immunogenicity, and easy for administration. However, the greatest advantage has been offered by the well-characterized molecular structures of target viruses which enable investigators to manipulate the viral cDNA genome with a recombinant DNA technique even with RNA viruses, as to produce recombinant progeny viruses (Rolph, M. S. and I. A. Ramshaw., *Curr. Opion. In Immunology* 9:517–524(1997)). The principal idea is to insert the exogenous insert nucleotide sequence encoding the desired foreign antigen into the attenuated viral genome without altering the viability of the virus. Theoretically, recombinant viruses can be used as an efficient recombinant vaccine, since the inserted genes can be replicated, expressed and packaged along with the viral genome, subsequently leading to induce immune responses not only to the parental viruses but also to the introduced foreign antigens.

The utility of this vaccine approach, however, has been largely constrained by several factors such as a limitation of an insert size, far reduced replication capacity, genetic instability, or a recurrence of the pathogenicity of the parental or recombinant viruses.

Many attempts have been made to manipulate the poliovirus (PV) as a favorable vaccine vector because of its attractive characteristics of safe usage, low cost, convenient administration, and long-lasting protective immunity in both mucosal and systemic immune responses, which have been established for decades. However, One of the most serious obstacles for a wide application of recombination poliovirus as an effective live viral vaccine vector has been the genetic instability of the recombinant virus.

Poliovirus, as a member of Picornaviridae, is a nonenveloped, positive-sense single-stranded RNA virus containing 7.44 kb of RNA genome. The genome contains an internal ribosomal entry site (IRES) followed by a single open reading frame (ORF) encoding a long polyprotein. The IRES element controls the expression of the polyprotein that is subsequently cleaved into several structural and nonstructural proteins by three kinds of virus-encoded proteases ($2A^{pro}$, $3C^{pro}$, and $3CD^{Pro}$). A major viral protease, $3C^{pro}$, and its precursor, $3CD^{pro}$, cleave the polyprotein at a specific site (AXXQ/G) within the expressed polyprotein, while a minor protease, $2A^{pro}$, cleaves the polyprotein at the junction between the P1 and P2 regions. Exactly 60 copies of each of four different capsid proteins (VP1, VP2, VP3, and VP4) are assembled into a rigid icosahedral viral capsid that concomitantly encapsidates the viral genome.

The polyprotein fusion strategy, one of the strategies for poliovirus-based vaccine developments, was directed at fusing the foreign insert to either at N-terminus or at the junction between the capsid proteins and nonstructural proteins (P1/P2) in the long polyprotein with an artificial cleavage site for poliovirus-specific proteases (Andino, R., D. et al., *Science* 265:1448–1451(1994) and U.S. Pat. No. 5,965,124). Accordingly, the foreign insert is cleaved-off by one of proteases and remains as a free form in the cytoplasm after being translated together with the viral proteins. A number of Mahoney-vector-based recombinant polioviruses were constructed by this strategy, and were demonstrated for their humoral, cellular, or mucosal immunogenicity against introduced exogenous antigens (Crotty, S., et al, *J. Virol.* 73:9485–9495(1999); and Mandl, S. et al., *Proc. Natl. Acad. Sci, USA* 95:8216–8221(1998)).

However, the plausibility of this strategy was challenged by the genetic instability of the recombinant viruses (Tang, S., et al, *J. Virol.* 71:7841–7850(1997); Mueller, S., and E. Wimmer., *J. Virol.* 72:20–31(1998)). Previous reports have suggested that the genetic instability of the rec-PV would be associated with the insert size limitation and/or genetic recombination within intra- (Tang, S., et al, *J. Virol.* 71:7841–7850(1997)) or between inter-sequences during minus-strand synthesis (Mueller, S., and E. Wimmer., *J. Virol.* 72:20–31(1998); Wimmer, E., et al, *Annu. Rev. Genet.* 27:353–436(1993)). Nevertheless, a clear molecular mechanism controlling insert stability has not been well established.

Consequently, there is a need of a novel strategy to overcome the shortcomings of the poliovirus vector systems aforementioned.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

To be free from shortcomings of the poliovirus vector systems, in particular, genetic instability of the foreign insert integrated into the recombinant polioviruses, the present inventors have examined potential factors governing genetic stability of foreign insert by constructing and exploiting many different recombinant polioviruses, which contain a series of different original or sequence-adjusted foreign inserts. From these experiments, we have accomplished present invention that i) the insert genetic stability is strongly associated with the G/C contents and its distribution patterns within the size limitation, and ii) the insert genetic stability can be markedly enhanced by increasing the G/C contents of the foreign insert.

Accordingly, it is an object of this invention to provide a method for improving a genetic stability of a foreign insert nucleotide sequence in a recombinant single-stranded RNA virus vector.

It is another object of this invention to provide a method for constructing a recombinant single-stranded RNA virus containing a foreign insert nucleotide sequence with improved genetic stability.

It is still another object of this invention to provide a recombinant single-stranded RNA virus comprising a foreign insert nucleotide sequence with improved genetic stability.

It is further object of this invention to provide a recombinant poliovirus comprising a foreign insert nucleotide sequence with improved genetic stability.

It is still further object of this invention to provide a method for construction of sequence-adjusted or artificially synthesized foreign inserts using template/ligation-free PCR method.

It is another object of this invention to provide a vaccine composition comprising a recombinant single-stranded RNA virus.

Other objects and advantages of the present invention will become apparent from the detailed description to follow taken in conjugation with the appended claims and drawings.

BRIEF DESCRIPTION OF THE DRAWINGS

FIG. 1 represents a genetic map of Sabin 1-based RPS-Vax vector used for constructing a recombinant poliovirus. RPS-Vax genome contains multiple cloning site (MCS) and 3C-protease cutting site at the N-terminal end of the long polyprotein.

In FIGS. 3a–3c, the symbol in parentheses next to the name of each insert represents the group to which it belongs (described in FIG. 4) and the insert specificity described in Table 1. M; 100 bp size marker, S; poliovirus Sabin 1, R; RPS-Vax vector-derived virus, C; insert-containing recombinant plasmid. The numbers indicate the passage cycle of each rec-PV. The bar and arrowhead indicate the original and truncated form of the inserts, respectively.

FIG. 5a shows the adjustment of a G/C content of SIV env-108 to prepare SIV env-108/M. The bases below the nucleotide backbone indicate the nucleotide substitutions for SIV env-108/M.

FIG. 5b is a photograph showing RT-PCR analysis demonstrating a genetic stability of SIV env-108 and its sequence-adjusted form, SIV env-108/M integrated into RPS-Vax. The percentage values in the parentheses represent the G/C content of the insert.

FIG. 5c shows the adjustment of a G/C content of SIV gag-100 to prepare SIV gag-100/M. The bases below the nucleotide backbone indicate the nucleotide substitutions for SIV gag-100/M.

FIG. 5d is a photograph showing RT-PCR analysis demonstrating a genetic stability of SIV gag-100 and its sequence-adjusted form, SIV gag-100/M integrated into RPS-Vax. The percentage values in the parentheses represent the G/C content of the insert.

FIG. 9 illustrates PVm-150/M sequence designed in accordance with this invention. The white and gray boxes with solid lines indicate the amino acid repeats of the VP1 epitope of poliovirus type 2 and type 3, respectively. The box with the dotted line indicates the 5 amino acid-repeats. The backbone is the nucleotide and the derived amino acid sequences of PVm-150. The bases in bold letters below the nucleotide backbone indicate the nucleotide substitutions for PVm-150/M.

FIG. 10 illustrates 8 primers used for template/ligation-free PCR amplification of the nucleotide sequence encoding PVm-150/M. Primers 1, 3, 5 and 7 are sense and primers 2, 4, 6 and 8 are antisense.

FIG. 13 is a photograph showing RT-PCR results demonstrating in vivo genetic stability of the insert sequence, PVm-150 or PVm-150/M integrated into RPS-Vax using Tg-PVR mice. PVR-transgenic mice were inoculated intra-cerebrally (ic) with rec-PV containing the original (PVm-150) and the sequence-adjusted (PVm-150/M) hetero-multimeric insert, respectively. Every day viruses were recovered from the spleen of each inoculated mouse, and were followed by a single-round amplification in HeLa cells. Viruses recovered from the passages in vivo were examined for their genetic integrity by RT-PCR. C denotes insert-containing recombinant plasmid. The number means the day after p.i. on which the rec-PV was recovered. The bar and arrow indicate the intact and the truncated form of inserts, respectively, which were generated during the replication of rec-PV in vivo.

DETAILED DESCRIPTION OF THIS INVENTION

Figure 2:
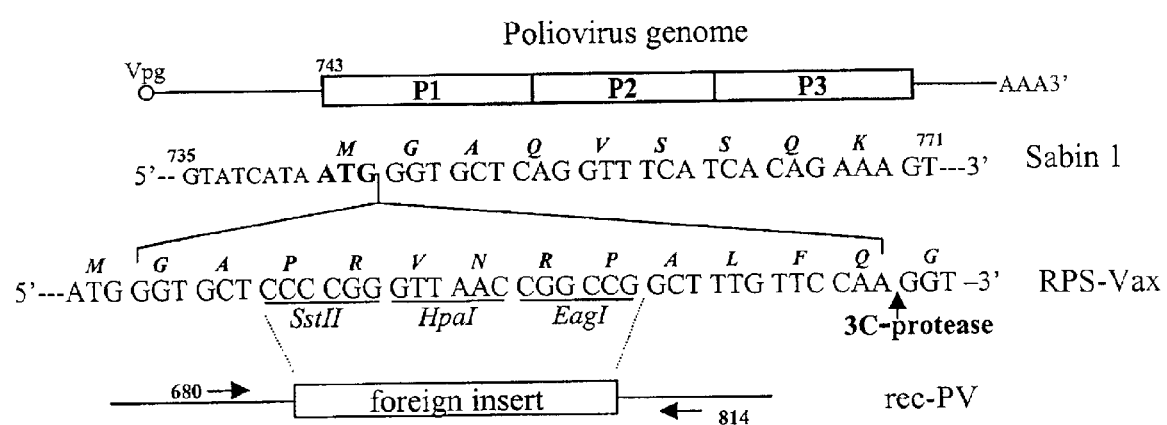
FIG. 2 shows a cloning scheme of foreign insert into RPS-Vax system to produce recombinant poliovirus. Foreign insert, integrated into the MCS, can be easily detected by RT-PCR with the primer set indicated by arrows.
Figure 3A:
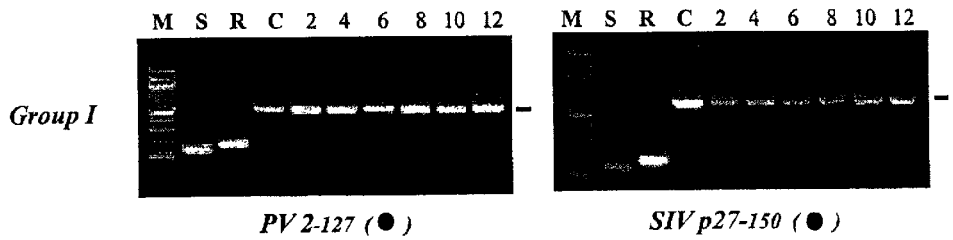
FIG. 3a is a photograph showing RT-PCR analysis demonstrating a genetic stability of the foreign insert, PV 2-127 or SIV p27-150 integrated into RPS-Vax.
Figure 3B:
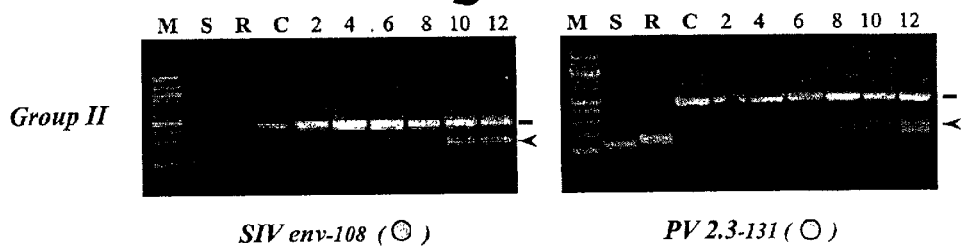
FIG. 3b is a photograph showing RT-PCR analysis demonstrating a genetic stability of the foreign insert, SIV env-108 or PV 2.3-131 integrated into RPS-Vax.
Figure 3C:
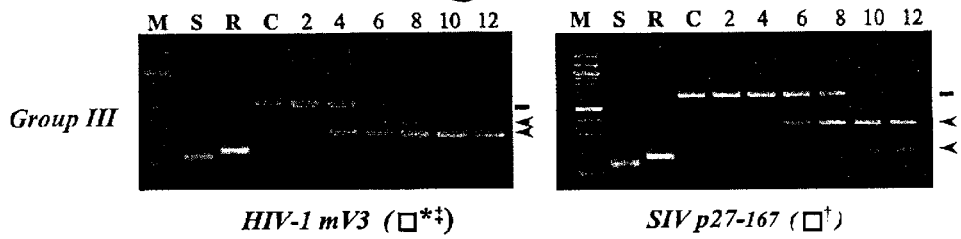
FIG. 3c is a photograph showing RT-PCR analysis demonstrating a genetic stability of the foreign insert, HIV-1 mV3 or SIV p27-167 integrated into RPS-Vax.
Figure 3D:
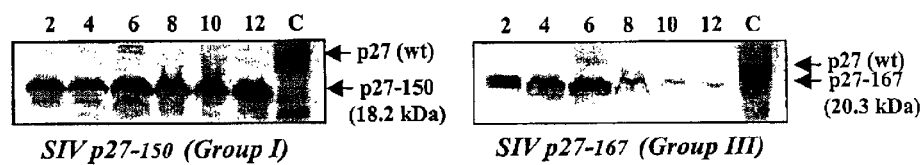
FIG. 3d is a photograph showing Western blot analysis demonstrating a protein stability of the insert sequence, SIV p27-150 or SIV p27-167 integrated into RPS-Vax. The numbers indicate the passage cycle of the rec-PV to be infected into HeLa cells. Rec-PV-infected HeLa cell lysates and control SIV (C) were screened by Western blotting with monkey anti-SIV serum. Arrows indicate the wild type p27 of SIV and recombinant p27 expressed from rec-PV.

One of the most important obstacles for constructing a single-stranded recombinant RNA virus, in particular, poliovirus, is the genetic instability of a foreign insert nucleotide sequence. The genetic stability of foreign insert has been predicted with difficulty from the sequence and had to be determined empirically. It has been regarded that the application of the recombinant RNA virus including vaccine would be much expedited if the stability of the given insert could be assessed prior to the experimental onset. For this purpose, the inventors have examined potential factors governing stability within the insert foreign gene, using recombinant viruses constructed with a series of different antigens. Based on this study as well as others, the inventors have established that a nucleotide composition of the insert sequence is a major determinant of the genetic stability.

Accordingly, in one aspect of the present invention, there is provided a method for improving a genetic stability of a foreign insert nucleotide sequence in a recombinant single-stranded RNA virus vector, which comprises performing a mutagenesis of the foreign insert nucleotide sequence (a) to provide even distribution of G/C content throughout the overall foreign insert nucleotide sequence and/or (b) to increase G/C content of the foreign insert without substantially causing amino acid substitutions.

The term used herein "genetic stability of insert (foreign) sequence" refers to that the insert sequence integrated into a single-stranded recombinant RNA virus, e.g., recombinant poliovirus, is stably maintained in insert-containing recombinant RNA virus during consecutive passage, generally, at least $4^{th}$ passage, preferably, at least $8^{th}$ passage, more preferably, at least $10^{th}$ passage and most preferably, at least $12^{th}$ passage. The term used herein "passage stability" is the same meaning as "genetic stability". If the foreign insert nucleotide sequence encodes certain antigen and exhibits a genetic stability in recombinant RNA virus (e.g. poliovirus), it can be expressed to give the antigen inducing immune response during consecutive passages. The genetic stability include, in a broader sense, protein stability encoded by the insert sequence.

The term used herein "even distribution of G/C content", refers to a G/C distribution pattern without showing any local A/T-rich region.

According to the invention, the genetic stability of the foreign insert nucleotide sequence integrated into a recombinant virus is accomplished by performing a mutagenesis of the foreign insert nucleotide sequence to provide even distribution of G/C content throughout the overall foreign insert nucleotide sequence. The mutagenesis should not lead to a substantial change of amino acid sequences encoded by the insert. For example, if the foreign insert codes for a polypeptide or a protein covering antigenic determinant sites, the mutagenesis should not be substantially detrimental to its antigenicity.

As demonstrated in Examples below, local A/T-rich region in insert sequence causes genetic instability of the foreign insert, thereby promoting the site-specific deletion of the neighboring region of the insert integrated into the recombinant virus. Substitution of local A/T-rich region with G/C-rich codon of the same amino acid renders the insert to have genetic stability.

The term used herein "local" along with A/T-rich region refers to a region of certain nucleotide sequence being, generally, about 60 bp in size, preferably about 50 bp in size, more preferably about 40 bp in size and most preferably about 30 bp in size. In addition, the term used herein "A/T-rich region" refers to a region having G/C content, generally, less than 40%, preferably, less than 35%, more preferably, less than 30% and most preferably, less than 25%. In this respect, according to preferred embodiment of this invention, the increment of a G/C content at local A/T-rich region means that the local A/T-rich region in size of about 30 bp with G/C content of less than 25% is rendered to have G/C content of more than 40%.

In the present invention, it is general that a higher G/C content avoids local A/T-rich region. Therefore, according to this invention, the genetic stability of insert is accomplished by increasing G/C content of the foreign insert sequence without substantially causing amino acid substitutions. According to preferred embodiment of this invention, the insert nucleotide sequence mutated for increasing G/C content is rendered to have the G/C content of more than 30%, more preferably, more than 40%.

In a preferred embodiment, the insert nucleotide sequence carried in recombinant RNA virus, in particular, poliovirus, has a size of less than 500 bp, more preferably, less than 480 bp and most preferably, less than 450 bp. In the case of poliovirus, it is assumed that the size limitation is ascribed to a limited packaging capacity of virus.

According to this invention, the mutagenesis without substantially causing amino acid substitutions includes not only the mutagenesis without any amino acid substitution but also the mutagenesis that results in a change of amino acids but does not cause loss of a function of polypeptide encoded by the insert, e.g., antigenicity. In preferred embodiment, the mutagenesis is performed using codon degeneracy by silent mutation (Crick, F. H. et al., *Nature*, 192:1227(1961)). The term "silent mutation" used herein refers to a mutation that results in a mutant codon specifying the same amino acid as did the original codon (owing to the degeneracy of the genetic code), which has substantially the same meaning as same-sense mutation.

The silent mutation can be performed by the methods known to one skilled in the art including site-directed mutagenesis and cassette mutagenesis. The mutagenesis can be readily performed by PCR-mutagenesis technique using appropriate primers.

According to preferred embodiment of this invention, the recombinant single-stranded RNA virus vector is derived from poliovirus, yellow fever virus, Venezuelan equine encephalitis virus, rubella virus or Coxsackie virus. More preferably, the recombinant single-stranded RNA virus vector is derived from poliovirus including poliovirus type 1 (Mahoney), poliovirus type 2 (Lansing) and poliovirus type 3 (Leon). It is more advantageous that the poliovirus is a live attenuated strain including poliovirus Sabin type 1, poliovirus Sabin type 2 or poliovirus Sabin type 3. Most preferably, the poliovirus is poliovirus Sabin type 1 which has been reported to show the lowest incidence of back mutation to a pathogenic wild type.

According to this invention, the foreign insert nucleotide sequence, for example, encodes a polypeptide or a protein antigen originated from organisms including bacterium, virus, fungus and eukaryotic parasites. The most prominent utility of the present method is an application to preparing the foreign insert derived from viruses. According to preferred embodiment, the foreign insert nucleotide sequence encodes a polypeptide or a protein antigen of an infectious virus selected from human immunodeficiency virus (HIV), simian immunodeficiency virus (SIV), hepatitis A virus (HAV), hepatitis B virus (HBV), hepatitis C virus (HCV), human papilloma virus (HPV), herpes simplex virus (HSV), different serotypes of poliovirus, rotavirus, influenza virus and epidemic hemorrhagic fever virus. More preferably, the foreign insert is a polypeptide or protein antigen covering major or minor antigenic determinant sites (i.e., epitopes). Some of the foreign insert contains dimer or multimer of the antigenic epitope. In the case of dimeric or multimeric insert, it is considerable that the repeated sequences is likely to induce genetic instability of the insert, probably due to the homologous recombination-mediated internal deletion during virus replication, as reported previously (Logg, C. R. et al., *J. Virol.*, 75:6989; and Pavelitz, T. et al., *EMBO J.* 14:169(1995)). According to the preferred embodiment of this invention, the dimeric or multimeric inserts are designed to consist of different monomers which have different nucleotide sequences to one another even though encoding the same amino acid sequence. In the present invention, the dimeric or multimeric foreign insert comprises homo/hetero-dimmer or homo/hetero-multimer.

The foreign insert prepared according to the present method is likely to induce a compact conformation of RNA transcript, followed by facilitating encapsidation of the recombinant v-RNA transcript into a rigid viral capsid, finally resulting in remarkable improvement of the genetic stability of a recombinant virus.

In another aspect of this invention, there is provided a method for constructing a recombinant single-stranded RNA virus containing an insert nucleotide sequence, which comprises the steps of: (a) preparing the foreign insert nucleotide sequence which has an even distribution of G/C content throughout the overall foreign insert nucleotide sequence and/or has a G/C content of more than 30%; and (b) introducing the foreign insert into a viral genome of a parent RNA virus to construct the recombinant RNA virus, wherein the introduction of the foreign insert does not disrupt the proliferation of the recombinant RNA virus.

The common descriptions between the method for improving a genetic stability and the method for constructing a recombinant virus of this invention are abbreviated in order to avoid the complexity of this specification leading to undue multiplicity.

According to preferred embodiment, the step of preparing the insert nucleotide is performed by the method for improving a genetic stability of the insert as described.

Alternatively, the step of preparing the foreign insert nucleotide sequence is performed by selecting the foreign insert nucleotide sequence from a natural-occurring nucleotide sequence, in which the selected nucleotide sequences has an even distribution of G/C content throughout the overall foreign insert nucleotide sequence and/or having a G/C content of more than 30%. For example, from a variety of epitopes found in many pathogens (e.g. HIV p24, HIV gp120, HIV env, SIV env, SIV gag and HCV core), a particular nucleotide region can be selected to meet the G/C criteria of this invention. As exemplified in Examples, env gene derived from HIV-1 carried in the recombinant poliovirus exhibits a various genetic stability depending on the selected regions.

According to preferred embodiment of this invention, the recombinant single-stranded RNA virus includes, but not limited to, poliovirus, yellow fever virus, Venezuelan equine encephalitis virus, rubella virus and Coxsackie virus.

More preferably, the recombinant single-stranded RNA virus is a poliovirus including poliovirus type 1 (Mahoney), poliovirus type 2 (Lansing) and poliovirus type 3 (Leon). It is more advantageous that the poliovirus is a live attenuated strain including Sabin poliovirus type 1, Sabin poliovirus type 2 or Sabin poliovirus type 3. Most preferably, the poliovirus is Sabin poliovirus type 1.

According to this invention, the insert nucleotide sequence, for example, encodes a polypeptide or a protein antigen selected from the group consisting of bacterial polypeptide antigens, viral polypeptide antigens, fungal polypeptide antigens and eukaryotic parasite polypeptide antigens. The most prominent utility of the present method is an application to construction of replication-competent recombinant viral vaccines. Therefore, according to preferred embodiment, the insert nucleotide sequence encodes a polypeptide or a protein antigen of an infectious virus including human immunodeficiency virus, simian immunodeficiency virus, hepatitis A virus, hepatitis B virus, hepatitis C virus, human papilloma virus, herpes simplex virus, poliovirus, rotavirus, influenza virus and epidemic hemorrhagic fever virus, but not limited to these. More preferably, the foreign insert nucleotide is a polypeptide or a protein antigen covering major antigenic determinant sites. Some of the foreign insert contains dimer or multimer of the major antigenic epitope. According to preferred embodiment of this invention, the dimeric or multimeric foreign insert comprises monomers that have substantially the same amino acid sequence but a different nucleotide sequence each other in order to avoid anticipated internal deletion.

The mutagenesis performed in the method should not lead to a substantial change of amino acid sequences encoded by the insert. Increasing G/C content of local A/T-rich region can provide even distribution of G/C content of the insert, resulting in the enhancement of the insert genetic stability. Therefore, according to this invention, the genetic stability of foreign insert nucleotide is accomplished by increasing G/C content of the insert sequence without substantially causing amino acid substitutions. According to preferred embodiment of this invention, the insert nucleotide sequence mutated for increasing G/C content is rendered to have the G/C content of more than 30%, more preferably, more than 40%.

In a preferred embodiment, the insert nucleotide sequence carried in recombinant RNA virus, in particular, poliovirus, has a size of less than 480 bp, more preferably, less than 450 bp.

In preferred embodiment, the mutagenesis is performed using codon degeneracy by silent mutation. The silent mutation can be performed by the methods known to one skilled in the art including site-directed mutagenesis and cassette mutagenesis. The mutagenesis can be readily performed by PCR-mutagenesis technique using appropriate primers.

In still another aspect of this invention, there is provided a recombinant single-stranded RNA virus comprising an insert nucleotide sequence, characterized in that the recombinant single-stranded RNA virus is constructed by the method as described above.

The common descriptions between the methods and the recombinant virus of this invention are abbreviated in order to avoid the complexity of this specification leading to undue multiplicity.

Exemplified recombinant poliovirus of this invention comprises (a) a genomic nucleotide sequence of a parent poliovirus; (b) an additional polioviral cleavage site; and (c) the foreign insert nucleotide sequence, wherein the foreign insert nucleotide sequence is introduced into the viral genome of a parent poliovirus without disrupting the viral infection and proliferation, and a poliovirus protease also acts on the additional cleavage site so that the polypeptide or protein antigen encoded by the foreign insert nucleotide sequence is released from a polyprotein precursor of the recombinant poliovirus.

The exemplified recombinant poliovirus vector is based on polyprotein fusion strategy (Andino, R., D. et al., *Science* 265:1448–1451(1994) and U.S. Pat. No. 5,965,124). In addition, the inventors have developed the polyprotein fusion strategy using poliovirus Sabin 1-based vaccine vector (hereinafter referred to as "RPS-Vax", see WO 99/07859). Insert-containing RPS-Vax is fully described in Examples.

According to preferred embodiment, the additional (exogenous) insert cleavage site is one for poliovirus-specific 3C protease or 2A protease.

The insert nucleotide sequence can be introduced into a various sites of polioviral genome unless the introduction is detrimental to replication of poliovirus. For example, the sites suitable for the introduction of insert include 5'-terminal region, the junction between Vp1 and 2A coding regions, the junction between 2A and 2B coding regions, and the junction between 2C and 3A coding regions.

It is common that the foreign insert of epitope multimer comprising repetitive amino acid sequence are designed to enforce the immunogenicity of a specific epitope. However, the repeated sequence may cause internal deletion for the foreign inserts during serial passages. According to this invention, the foreign inserts comprising epitope multimers are newly designed to avoid the repeats of nucleotide sequence by adjusting nucleotide sequence within the range of silent mutation.

For preparing multimeric insert, which is designed to have multiple silent mutations to increase a genetic stability according to this invention, the inventors have developed a feasible template/ligation-free PCR method.

Accordingly, in further aspect of this invention, there is provided a method for amplifying a nucleotide sequence using template/ligation-free PCR method, which comprises the steps of: (a) preparing a plurality of DNA fragment serving as both template and primer, in which the DNA fragments are designed by dividing the entire nucleotide sequence of interest into several fragments with different complementary region so that one segment is used as a template while being primed by the other; (b) mixing the DNA fragments in such a manner that the DNA fragments corresponding to both ends of a final nucleotide sequence, which is also used in amplification step, has a higher concentration than the other DNA fragments; (c) preparing a full length of the nucleotide sequence of interest by PCR for 20–40 sec at 92–96° C. (denaturation), for 20–40 sec at 25–40° C. (annealing) and for 40–70 sec at 68–75° C. (extension); (d) amplifying the nucleotide sequence of interest by PCR for 20–40 sec at 92–96° C. (denaturation) and 40–70 sec at 68–75° C. (annealing and extension).

The amplifying method is clearly illustrated in FIG. 9. In this method, primer design is very critical, example of which is described in Example V-1 and illustrated in FIG. 11. Intermediates even though generated in maturation step (the step (b)) are rarely amplified in final amplification step, due to a higher annealing temperature and a shortage of internal primers in concentration as compared to those of external primers that are complementary to both ends of the PCR product, repectively. Therefore, according to the present method, the nucleotides sequence of interest can be yielded as a sole final product without adding template DNA and ligation step.

According to preferred embodiment, the concentration ratio of the primers corresponding to both ends of final PCR product to the other primers is 1:3–1:8, more preferably, 1:3–1:7 and most preferably, 1:6.

In preferred embodiment, the complementary regions of the junctional primers have 8–20 bp in length and G/C content of more than 35% and more preferably, 10–17 mer of length and G/C content of more than 40%. It is preferred that the primers corresponding to both ends of the final product have a cloning site consisting of restriction enzyme sites.

In still further aspect of this invention, there is provided a vaccine composition comprising (a) a recombinant single-stranded RNA virus carrying a foreign insert nucleotide sequence encoding antigen derived from pathogen and (b) a pharmaceutically acceptable carrier.

In preferred embodiment, the pathogen is an infectious virus and antigen is a major epitope-containing peptide or protein as described above.

In the vaccine composition of this invention, the pharmaceutically acceptable carrier may be conventional one for formulation, including lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methylhydroxy benzoate, propylhydroxy benzoate, talc, stearic acid, magnesium and mineral oil, but not limited to. The pharmaceutical compositions of this invention, further may contain wetting agent, sweetening agent, emulsifying agent, suspending agent, preservatives, flavors, perfumes, lubricating agent, or mixtures of these substances.

The pharmaceutical compositions of this invention may be administered orally or parenterally. The oral administration is the most preferable mode for the present compositions.

The correct dosage of the pharmaceutical compositions of this invention will vary according to the particular formulation, the mode of application, age, body weight and sex of the patient, diet, time of administration, drug combinations and reaction sensitivities. It is understood that the ordinary skilled physician will readily be able to determine and prescribe a correct dosage of this pharmaceutical compositions. For example, it is preferable that the vaccine composition comprising a recombinant Sabin 1 strain is administrated at dose of less than $10^6$ $TCID_{50}$.

According to the conventional techniques known to those skilled in the art, the pharmaceutical compositions of this invention can be formulated with pharmaceutical acceptable carrier and/or vehicle as described above, finally providing several forms including a unit dosage form. Non-limiting examples of the formulations include, but not limited to, a solution, a suspension or an emulsion, an extract, an elixir, a powder, a granule, a tablet, a capsule, emplastra, a liniment, a lotion and an ointment.

The vaccine compositions of this invention are significantly effective in inducing immune response (humoral, cellular or even mucosal immunity) against exogenous antigen.

The following specific examples are intended to be illustrative of the invention and should not be construed as limiting the scope of the invention as defined by appended claims.

EXAMPLES

Materials and Methods

Cells and Viruses

HeLa cells (HeLa S3 from ATCC) were used for transfection experiments and poliovirus propagation. HeLa cells were grown in Dulbeco's Modified Eagle's Medium (DMEM, GIBCO/BRL) supplemented with 10% fetal calf serum (GIBCO/BRL), 1× penicillin-streptomycin (GIBCO/BRL), 50 μg/ml of gentamicin. Mahoney (wild-type neurovirulent strain), Sabin 1 (attenuated strain of Mahoney) and recombinant polioviruses were produced by transfection of HeLa cell monolayers with viral RNAs, which were transcribed from reconstructed or original cDNAs. Recombinant cDNAs and their RNA transcripts are described below. Wild-type polioviruses, Lancing and Leon, were obtained from ATCC.

Mice

Human poliovirus receptor-transgenic (ICR-PVR-Tg21) mice (Koike, S., C. Taya, T. Kurata, S. Abe, I. Ise, H. Yonekawa, and A. Nomoto. 1991. Transgenic mice susceptible to poliovirus. *Proc. Natl. Acad. Sci. USA* 88:951–955) were kindly provided by Dr. A. Nomoto, University of Tokyo, Japan. These mice were bred and maintained in the Animal Resources Center at the Korea Research Institute of Bioscience and Bioengineering under specific pathogen-free conditions.

Materials

All enzymes used in this experiment were purchased from New England Biolabs (NEB, Beverly, Mass., USA), GIBCO/Bethesda Research Laboratory (GIBCO/BRL, Gaithersberg, Md., USA), Bio-Rad (Bio-Rad, Hercules, Calif., USA), Boehringer Mannheim Biochemicals (BMB, Mannheim Germany), Bioneer (Seoul, Korea). Cell culture media and serum were obtained from GIBCO/BRL. *Echerichia coli* JM109 (Promega, Madison, Wis., USA) and XL1-blue (Stratagene, La Jolla, Calif., USA) were used for transformation and propagation of plasmids. CJ236 and MV1190 for site-specific insertion and mutagenesis were purchased from Bio-Rad (Hercules, Calif., USA).

Recombinant Plasmid

The RPS-Vax system, developed by the inventor, consists of pTZ-18/R (Pharmacia Biotech, Uppsala, Sweden) as a backbone and full-length Sabin 1 recombinant cDNA, containing multiple cloning sites and a viral protease recognition site at the N-terminal end of the Sabin 1 polyprotein (Jung, H. R., and Y. S. Bae. 1998. Poliovirus Sabin 1 as a live vaccine vector: Expression of HIV-1 p24 core protein. *J. Biochem. Mol. Biol.* 31: 432–443). This system was mainly used for cloning and production of recombinant PV. The Sabin 1 cDNA, pVS(1)IC-0(T), was kindly provided by Dr. A. Nomoto (Institute of Medical Science, The University of Tokyo, Minato-ku, Japan). The Mahoney cDNA, pEV104 and pT7PV1-5, were kindly provided by Dr. E. Wimmer (State University of New York, Stony Brook, N.Y., USA). The HIV-1 (pHXB2 and $pSHIV_{89.6}$-3') and the SIV (pSIVmac239) cDNA clones were supplied by the NIH AIDS Research and Reference Reagent Program (Rockville, Md., USA). The cDNA clone (adw) of the Hepatitis B virus (HBV) was obtained from ATCC. The DNA clone of Hepatitis C virus (HCV) was kindly provided by Dr Y. C. Sung (Pohang University, Korea). The synthetic oligonucleotides were supplied by Bio-Synthesis, Inc. (Lewisville, Tex., USA) and Universal DNA, Inc. (Tigard, Oreg., USA), Genotech Co. (Daejeon, Korea) and BIO BASIC, Inc. (Canada).

Construction of Recombinant Poliovirus (Rec-PV) cDNAs

The DNA sequences coding for the various antigenic epitopes was amplified by PCR (Choi, B. K. et al., 2000. Prevention of encephalomyocarditis virus-induced diabetes by live recombinant Mycobacterium bovis bacillus Calmette-Guerin in susceptible mice. Diabetes 49:1459–1467) with primers designed to have SstII and EagI restriction sites at the 5' and 3' ends, respectively (SEQ ID Nos:25–95). The PCR products were purified and digested with SstII and EagI (NEB), and subcloned into the corresponding sites of the RPS-Vax as illustrated in FIG. 2. In the case of the multimeric concatamer epitope, the inventors designed the insert DNA by using the proper codon as specified in the general rules described in this specification. All of these plasmid constructs were tested for their capacity to produce progeny viruses by transfection experiments.

In vitro Transcription and Transfection of HeLa Cells

Plasmid DNAs were linearized with SalI (NEB) and purified by extraction three times with phenol-chloroform, followed by ethanol precipitation to minimize the contamination of RNase. One microgram of linearized plasmid DNA was transcribed in vitro with 5U/μl T7 RNA polymerase (NEB) in the reaction buffer (40 mM Tris-HCl, pH 8.0, 8 mM $MgCl_2$, 2 mM spermidine, 25 mM NaCl, 5 mM DTT, 1 U/μl RNasin, 2 mM dNTP) for 30 min at 37° C. Monolayers of HeLa cells ($3\times10^5$) were grown in 60 mm dishes. Less than 1 μg of RNAs were transfected into the cells by a DEAE-dextran procedure (Bae, Y. S. et al, 1993. Development of a recombinant RNA technique for the construction of chimeric RNA with a long poly(C) tract. *Nucleic. Acids. Res.* 21:2703–2708; and Kim, I. S. et al, 2000. Truncated form of importin alpha identified in breast cancer cell inhibits nuclear import of p53. *J. Biol. Chem.* 275:23139–23145). Cells were incubated until a full cytopathic effect (CPE) was observed, and a second passage of the supernatants was performed at this stage. Titers of viruses in the supernatant of these transfected cultures were determined by end-point dilution such as $TCID_{50}$ or a plaque assay on HeLa cell monolayers.

Virus Infection and One-Step Growth Curve

HeLa cell monolayers grown in 60 mm plates were infected with wild-type or recombinant polioviruses at an MOI of 10. The virus was allowed to adsorb to the cells for 1 h at 37° C. Unbound viruses were removed by washing twice with PBS, and 3 ml of pre-warmed DMEM containing 10% FEBS was added. The supernatants were collected every 3 h, and then titrated for the amounts of progeny viruses at each time after infection. The virus titers were determined by a $TCID_{50}$ assay.

Serial Passages, Viral RNA Extraction and Reverse Transcription (RT)-PCR

Each recombinant virus, generated from transfection of the HeLa cells with recombinant viral RNA transcript as described above, was consecutively introduced into the HeLa cells. In each passage, HeLa cell monolayers were infected with the recombinant virus harvested from the previous infection at an MOI of 10 as described above, and then cultured for 18 to 24 h. Supernatants were harvested as a virus source for each passage when a full CPE appeared. They were mixed with 4% PEG and 0.5M NaCl at a final concentration, and allowed to stand for 10 min at room temperature, and then precipitated by centrifugation for 10 min at 15,000 rpm. Viral RNA was extracted from the pellet with phenol-chloroform followed by ethanol precipitation. RT-PCR was performed for each v-RNA sample with Sabin 1 primers (680–697/sense; 5'-CAT TGA GTG TGT TTA CTC-3' and 797–814/antisense; 5'-GGT AGA ACC ACC ATA CGC-3') using a Pre-Mix RT-PCR kit (Bioneer Inc., Korea) by following instructions given in the vender's manual. PCR was performed for 25 cycles at 94° C. for 30 sec., 45° C. for 30 sec., and 72° C. for 45 sec. Amplified cDNA fragments were analyzed in agarose gel.

Western Blot Analysis

HeLa cells were infected with wild-type or rec-PVs at a MOI of 10 at each passage. Cells were harvested 18 h after infection, washed and resuspended with PBS, and then mixed with the same volume of 2×SDS-PAGE sample buffer (62.5 mM Tris-HCl, pH 6.8, 10% glycerol, 2% SDS, 1% β-mercaptoethanol, 0.03% bromophenol blue, and 0.01 mg/ml Xylene cyanol). After being boiled for 10 min, samples were applied to a SDS-12% polyacrylamide gel electrophoresis (PAGE) and then transblotted to a nitrocellulose membrane using a semi-dry gel transfer system (Bio-Rad). Blotted membranes were screened with monkey anti-SIV sera (kindly provided by Dr. G. Hunsmann, German primate Center, Gottingen, Germany) or mouse antisera obtained from the mouse immunized with specially designed recombinant proteins (BSA-conjugated PV2,3-specific epitope peptides) for this experiment (FIG. 13b). An ECL chemiluminescence detection kit (Amersham), or Alkaline phosphatase-conjugated secondary Ab and NBT/BCIP were used to detect the specific bands.

Rapid Synthesis of the Long Concatameric DNA by Template/Ligation-Free PCR

In order to make a hetero-multimeric epitope-concatamer that contains several multiple silent mutations, we have established a primer-annealing ligation-free PCR method by modification of the previous protocols (Khudyakov, Y. E et al, 1993. Synthetic gene for the hepatitis C virus nucleocapsid protein. *Nucleic. Acids. Res.* 21:2747–2754; Majumder, K. 1992. Ligation-free gene synthesis by PCR: synthesis and mutagenesis at multiple loci of a chimeric gene encoding ompA signal peptide and hirudin. *Gene* 116:115–116; and Wheeler, V. C. et al., 1996. Synthesis of a modified gene encoding human ornithine transcarbamylase for expression in mammalian mitochondrial and universal translation systems: a novel approach towards correction of a genetic defect. *Gene* 169:251–255). In principle, a long insert DNA can be synthesized by simple PCR without an original template DNA and an extra ligation step. The entire sequences of the designed PVm-150 and PVm-150/M were divided into 8 segments with 7 different complementary regions (CR), so that one segment was used as the template while being primed by the other. Each CR consists of 15 bases and more than 50% of G/C content. The strategy of the inventors consisted of two consecutive procedures—maturation and amplification (schematically illustrated in FIG. 9). As a maturation procedure, 5 rounds of denaturation (at 94° C. for 20 sec), annealing (at 43° C. for 20 sec), and polymerization (at 72° C. for 40 sec) steps were performed to anneal 8 DNA fragments (7.5 pmole each in 100 µl reaction buffer) into a full-length DNA. PCR amplification followed the reaction for 25 cycles at the conventional PCR condition (94° C. for 20 sec, and 72° C. for 1 min) in the presence of 45 pmole of both terminal segments as a primer set for preparation of full-length synthetic inserts. PVm-137/M and PVm-132/M inserts were also synthesized by following this protocol.

Recovery of Rec-PV from the Inoculated Tg-PVR Mice

Poliovirus receptor (PVR)-transgenic ICR mice 6 to 8 weeks old were inoculated intracerebrally with $10^7$ pfu of recombinant poliovirus using a microsyringe and specially designed 26/30 gauge needles. Mice were sacrificed daily after inoculation. The spleen was separated from each mouse, and homogenized using a Dounce homogenizer (15 strokes). The homogenates were centrifuged at 3000 rpm for 20 min and the supernatants were transferred into HeLa cell monolayers to recover the virus passed in vivo. They were tested for genomic integrity by RT-PCR, as described above.

RESULTS

Construction of Various Chimeric Viruses Using the RPS-Vax System

The inventors have constructed a number of PV recombinants by cloning foreign genes into the multiple cloning sites of the Sabin 1-derived RPS-Vax vector (Jung, H. R., and Y. S. Bae. 1998. Poliovirus Sabin 1 as a live vaccine vector: Expression of HIV-1 p24 core protein. *J. Biochem. Mol. Biol.* 31: 432–443). Foreign genes were derived from the region covering major antigenic determinant site in the structural proteins of other pathogenic viruses, including HIV, SIV, and hepatitis B and C viruses, as well as other PV strains.

The cDNA fragments coding for the exogeneous antigen used for construction of various chimeric polioviruses are: as monomer, SIV (Simian Immunodeficiency Virus) gag-100 (SEQ ID NO:1), SIV gag-100/M (SEQ ID NO:2), SIV gag-114 (SEQ ID NO:3), SIV p27-167 (SEQ ID NO:4), SIV p27-150 (SEQ ID NO:5), SIV env-108 (SEQ ID NO:6), SIV env-108/M (SEQ ID NO:7), HIV-1 env-98 (SEQ ID NO:8), HIV-1 env-98/M (SEQ ID NO:9), HIV-1 env-83 (SEQ ID NO:10), HIV-1 env-71 (SEQ ID NO:11), PV(poliovirus) 2-127 (SEQ ID NO:12), PV 2-118 (SEQ ID NO:13), PV 3-110 (SEQ ID NO:14), HCV core-160 (SEQ ID NO:15)

and HCV core-100 (SEQ ID NO:16); as heterodimer, PV 2.3-131 (SEQ ID NO:17), PV 2.3-112 (SEQ ID NO:18) and HBVcs (SEQ ID NO:19); as concatenate multimer, HIV-1 mV3 (SEQ ID NO:20) and HIV-1 PND8 (SEQ ID NO:21); and as designed multimer, PVm-150/M(SEQ ID NO:22), PVm-137/M(SEQ ID NO:23) and PVm-132/M(SEQ ID NO:24).

The cDNA fragments of the antigen coding region were individually synthesized or PCR-amplified, and then ligated into the multiple cloning sites of the RPS-Vax vector to produce a recombinant PV cDNA clone. Each clone was in vitro transcribed into recombinant viral RNA and then transfected into HeLa cells as described elsewhere (Bae, Y. S., Y. Kang, E. Ohtsuka, and J. W. Yoon. 1993. Development of a recombinant RNA technique for the construction of chimeric RNA with a long poly(C) tract. Nucleic. Acids. Res. 21:2703–2708), resulting in the production of recombinant PV.

The replication-competent recombinant viruses, as judged by the cytopathic effect of the transfected HeLa cells, and their biochemical characteristics are summarized in Table 1. Some of the recombinants were designed to have homo- or hetero-multimeric epitope-containing foreign insert to enhance the epitope-specific immune response or to elicit a dual or multi-immunogenicity by a single administration. We have constrained the overall size of the insert to less than 500 bases because inventors' repeated experiments revealed that the genetic stability of the RPS-Vax-based recombinant viruses decreases markedly with inserts greater than this size.

Among a variety of recombinant Sabin 1 vectors constructed, the vector carrying PVm-150/M was denoted as "RPS/OPV-150", deposited on Feb. 1, 2001 in International Depository Authority, the Korean Collection for Type Cultures and given accession number KCTC 0940BP.

The kinetics of RNA synthesis of replication-competent PV recombinants was almost similar to that of the control Sabin 1 (data not shown). However, the replication capacity of the recombinant viruses was a maximum of one log lower than that of the control Sabin 1 in the one step growth experiments (data not shown), as described previously (Jung, H. R., and Y. S. Bae. 1998. Poliovirus Sabin 1 as a live vaccine vector: Expression of HIV-1 p24 core protein. *J. Biochem. Mol. Biol.* 31: 432–443). Stable expression of the foreign antigens during the replication of the recombinant PV in HeLa cells was confirmed by Western blotting and radio-immunoprecipitation (RIP) analyses, using patients' sera, as well as either polyclonal or monoclonal antibodies against individual antigen. (Parts of the data are described in the following section.) In most cases, the immunoblotting analyses showed a single prominent band of a correctly processed polypeptide accompanied by a number of minor bands at higher molecular weights. These are likely due to the incomplete processing of fusion protein.

Each Recombinant PV Showed Different Genetic Stability Depending on Its Foreign Insert The genetic stability of each recombinant PV was examined by RT-PCR (and sequencing, if necessary,) and Western blotting for the foreign insert during the consecutive passages. The inventors have extended the number of passage cycles up to 12, because the lower number (<6) of passage cycles generally used in previous reports (Muller, S. et al., *J. Virol.* 72:20–31(1998); and Tang, S. et al., *J. Virol.* 71:7841–7850(1997)), was considered to be insufficient to draw any decisive conclusion about its stability. In each passage, the recombinant PV was harvested at full CPE, extracted by phenol-chloroform, and then subjected to the RT-PCR with Sabin 1 PCR primer sets, as shown in FIG. 2. The genetic stability of each recombinant was deduced from the gel pattern of PCR products in each of the passages. Based on its apparent genetic stability, the inventors have categorized the recombinant PV into 3 classes: stable (Group I), meta-stable (Group II), and unstable (Group III) recombinants (FIGS. 3*a*–3*c*).

Group I is the class that retains the intact insert without any truncated form of insert during the entire period of 12 consecutive passages. Recombinant PV carrying foreign genes, such as PV2-127 and SIV p27-150 (FIG. 3*a*), typically belongs to this group. This pattern of stability was observed in a total of 15 out of 24 different recombinants (63%). On the other hand, Group II is defined as the class that displayed the intact insert throughout the 12 passages, but the truncated form also appeared in the later stages. This pattern of stability was observed in three recombinants, containing an insert of SIV env-108 (monomeric), PV2,3-131 (hetero-dimeric) or HIV-1 PND8 (concatameric), respectively. As shown in FIG. 3*b*, the genomic integrity of the antigens, SIV env-108 or PV2.3-131, was stably maintained in the recombinant viruses during the early passages, but was slowly attenuated in the later cycles, as shown by the gradual accumulation of a shortened band (marked by an arrow in FIG. 3*b*). However, a major portion of the virus population still retained the intact insert during the entire 12 passages. Group III, on the contrary, is characterized as the class showing genetic instability during the 12 passages. In this class, the instability of the gene was so severe that an intact insert band disappeared rapidly in the later stages. This was shown in the recombinant containing HIV-1 mV3, tandem repeated V3 epitope, or SIV p27-167 (FIG. 3*c*). Three additional monomeric clones (HIV-1 env-98, HIV-1 env-71, and HCV core-160) belong to this group. The genetic deletions of unstable clones were site-specific and had progressed moderately.

Each recombinant PV expresses foreign insert during its replication in the infected cells. Therefore genomic stability should also be repeated in the protein expression. The inventors have examined the correlation between the genomic stability and its expression stability by Western blotting, using two different rec-PVs, RPS-Vax/SIV p27-150 and RPS-Vax/SIV p27-167. RPS-Vax/SIV p27-150 was genetically stable during the entire 12 passages, but the RPS-Vax/SIV p27-167, belonging to Group III in genomic stability, was not (FIG. 3*a*). Consistently, both recombinants showed similar patterns in expression stability, in the Western blot experiments with Monkey anti-$SIV_{mac}$239 serum (FIG. 3*d*), suggesting that the RT-PCR analysis would be enough to determine the genetic stability for each recombinant PV. Small protein bands which might have been expressed from the truncated inserts detected in RT-PCR (FIGS. 3*a*–3*c*), did not appear in the Western blot at the corresponding sites (FIG. 3*d*).

Genetic Stability of the Insert Associated with G/C Content

In order to determine the effect of the insert size on stability, inventors have examined the size of the foreign insert of each class of recombinants. The inventors found, surprisingly, that stability was not well correlated to the linear size of the insert in the range of 200 to 400 nucleotides (Table 1).

This finding led us to reconsider other potential factors influencing genetic stability of the insert. Given the genetic properties of PV and the deletion pattern of the recombinants, it is very likely that genetic stability is determined mainly by the encapsidation efficiency of the recombinant genome. It was presumed that the content of G/C provides a primitive guideline to measure the spatial compactness of the insert RNA. The G/C content may also be important for the flexibility of the tertiary structure of RNA.

Figure 4:
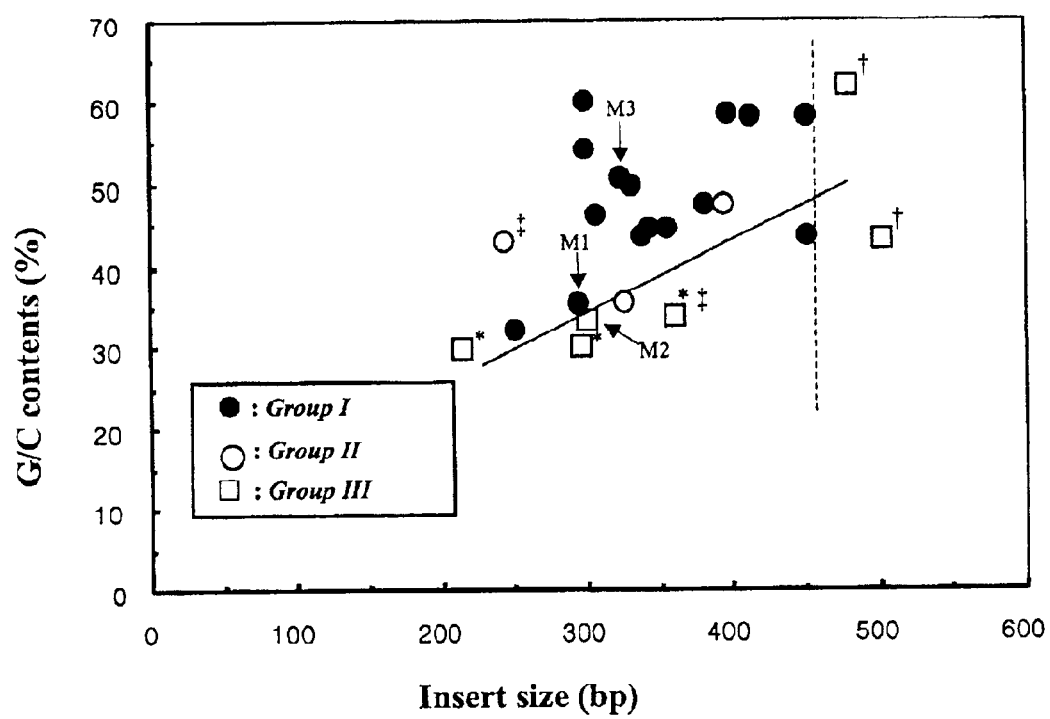
FIG. 4 is a diagram showing a correlation between the genetic stability of foreign insert and the G/C content and the size of the foreign insert. The genetic stability of each rec-PV, determined by RT-PCR, was illustrated in the diagram in association with insert size and G/C-contents. Each line represents the postulated limitations of acceptable insert size (---) and G/C contents (-) for stable passages of each rec-PV. *; A/T rich region-containing insert. ‡; insert containing multiple-epitope concatamer repeats. †; insert larger than the limit of acceptable size. M1: HIV-1 env-98/M. M2: SIVgag-100/M. M3: SIV env-108/M.

The inventors have investigated the G/C content of each RNA insert and then plotted each recombinant on the field of G/C-content and insert size to relate it to the apparent stability. As summarized in the diagram (FIG. 4), most of the stable inserts (Group I), except HIV-1 env-83, were found to have a G/C content higher than 40% and a size smaller than 400 bases. On the other hand, the inserts with a G/C content less than 30% seemed to be genetically unstable regardless of the insert size (HIV-1 env-71; 213 bp insert). These results suggest that the stable inserts would form a compact RNA conformation and readily be encapsidated into a rigid viral capsid.

To elucidate the correlation between the genetic stability of the rec-PV and G/C-content of the insert, inventors have adjusted 44 nucleotides on the sequence of the genetically unstable insert SIV env-108 to make it have a higher G/C content (SIV env-108/M) without any change in the amino acid sequence. As shown in FIG. 5b, the sequence-adjusted SIV env-108/M insert, having a higher G/C content (50.3%), completely recovered its genetic stability, while its original clone SIV env-108 (35.4%) was genetically unstable during the passages. These results were similarly repeated in the rec-PVs expressing HIV-1 p24 or Nef (data not shown). On the other hand, to confirm the correlation between the G/C content and genetic stability in another way, inventors have reduced the G/C content of the stable insert, and tested the genetic stability of the modified rec-PV. SIV gag-100 was genetically stable and its G/C content was 45% (Table 1). However, when the G/C content of the insert was reduced to 34% by replacing the 34 G or C sites with A/T on the entire nucleotide sequence (300 bp) without a change of amino acid sequence, the clone SIV gag-100/M lost its genetic stability as shown in FIG. 5d. These results strongly support inventors' hypothesis that the genetic stability of the rec-PV is strongly associated with the G/C content of the insert.

Whereas, inserts larger than 450 bp were also unstable, even though they had a higher G/C content of up to 62.3% (HCV core-160). This means that foreign inserts larger than 450 bp are not acceptable to the RPS-Vax vector system when producing genetically stable rec-PVs. Certainly, this delimitation of the insert can be maximally introduced in our strategy and is somewhat larger than the size limitation (10 kDa) in the Mahoney vector system, as addressed in the previous report (Mueller, S., and E. Wimmer. 1998. Expression of foreign proteins by poliovirus polyprotein fusion: analysis of genetic stability reveals rapid deletions and formation of cardioviruslike open reading frames. *J. Virol.* 72:20–31).

These results can be summarized in a manner that i) increasing the G/C content of an unstable insert augmented the genetic stability of its rec-PV, and ii) reducing the G/C content of a stable insert made the rec-PV lose its genetic stability during the passages. This suggests that a high G/C content might facilitate the packaging of recombinant viral RNA. The detailed mechanisms are still unknown, but the fact that the guanine base is able to pair with the uracil in addition to the normal G/C pairing within a single-stranded RNA (Heerschap, A., J. A. Walters, and C. W. Hilbers. 1986. Influence of the polyamines spermine and spermidine on yeast tRNAPhe as revealed from its imino proton NMR spectrum. *Nucleic. Acids. Res.* 14:983–998), might give more dynamic flexibility to the insert structure in the recombinant viral RNA, which results in an effective encapsidation, followed by the production of genetically stable rec-PVs.

Figure 6A:
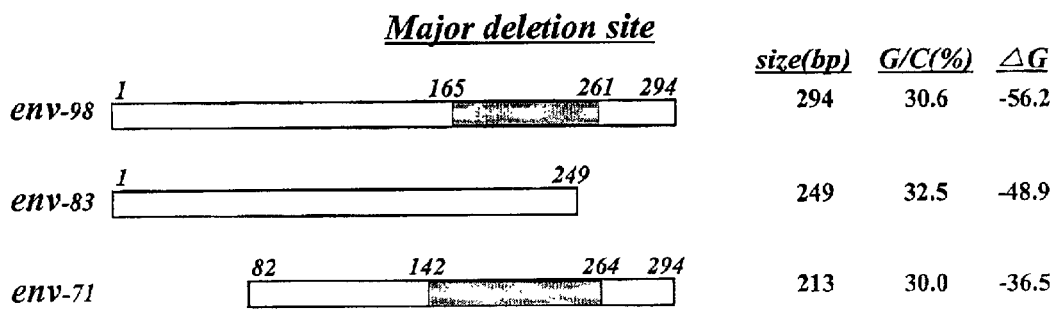
FIG. 6a represents the characteristics of the insert sequences, HIV-1 env-98, HIV env-83 and HIV-1 env-71. The solid box in the diagram indicates the major deletion site during the passages of the rec-PV. The numbering of the 294 bp corresponds to the sequence 787–1080 of HIV-1 envelop (env).
Figure 6B:
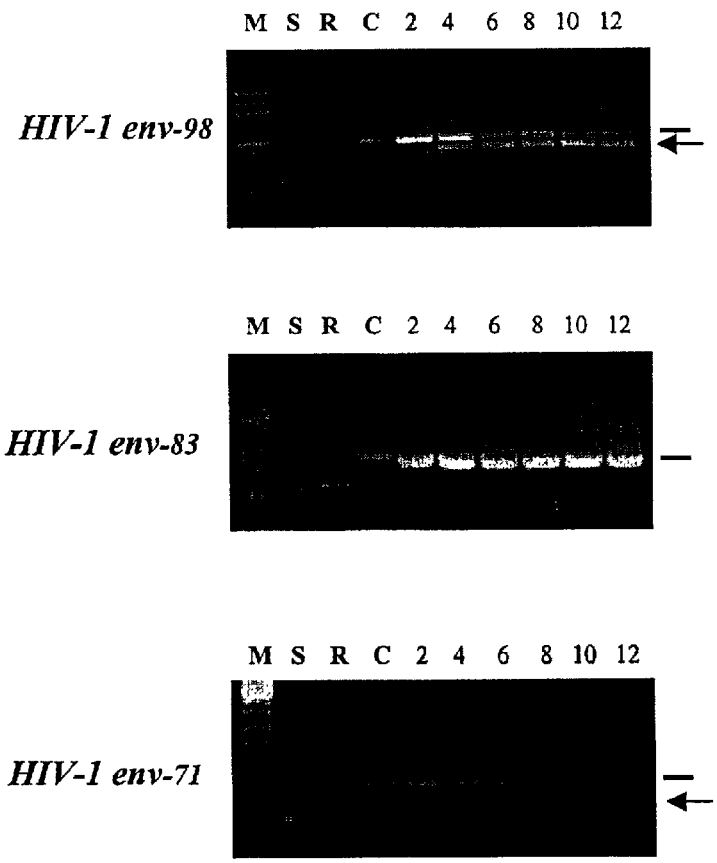
FIG. 6b is a photograph showing RT-PCR analysis demonstrating a genetic stability of each insert, HIV-1 env-98, HIV env-83 or HIV-1 env-71 integrated into RPS-Vax. M; 100 bp size marker, S; poliovirus Sabin 1, R; RPS-Vax vector-derived virus, C; insert-containing recombinant plasmid. The numbers represent the passage cycle of each rec-PV. The bar and arrow indicate the original and truncated bands of the insert, respectively.

Even Distribution of the G/C Content is Also Important for Overall Insert Stability Of particular interest was a result obtained from the comparative stability study of three inserts derived from an HIV-1 env gene. The three different inserts denoted by env-98, -83, and -71 were prepared to include the principal neutralizing domain of env gene (FIG. 6a). Only the env-83 insert displayed complete stability, while the other two inserts, env-98 and -71, showed prominent genetic instability with multiple discrete bands of truncated fragments (FIG. 6b) even though they had very similar G/C content (30–32.5%) (Table 1 and FIG. 6a). The inventors purified the major truncated fragment in RT-PCR, indicated by an arrow in FIG. 6b, from env-98 and env-71, and then subjected it to DNA sequencing to determine whether this deletion took place in a sequence-specific manner. The inventors identified that the regions of 165–261 and 142–264 (in base number) were deleted from env-98 and env-71 respectively, implying that the region between 165 and 261 was a common deletion site (FIG. 6a). Nevertheless, inventors could not find any short repeated sequences around the deletion site which might have caused internal deletion via nonhomologous RNA recombination mechanisms as suggested in the previous report (Mueller, S., and E. Wimmer. 1998. Expression of foreign proteins by poliovirus polyprotein fusion: analysis of genetic stability reveals rapid deletions and formation of cardioviruslike open reading frames. *J. Virol.* 72:20–31).

Particularly noteworthy however, is the fact that the terminal sequence commonly present at the 3' end of env-98 and env-71, but not env-83, is extremely A/T-rich, and the local G/C content is only 20% (FIG. 6a). Inventors speculated that the local A/T-rich sequence would be a potential cause for the marked genetic instability of the env-98 and env-71 inserts.

Figure 7A:
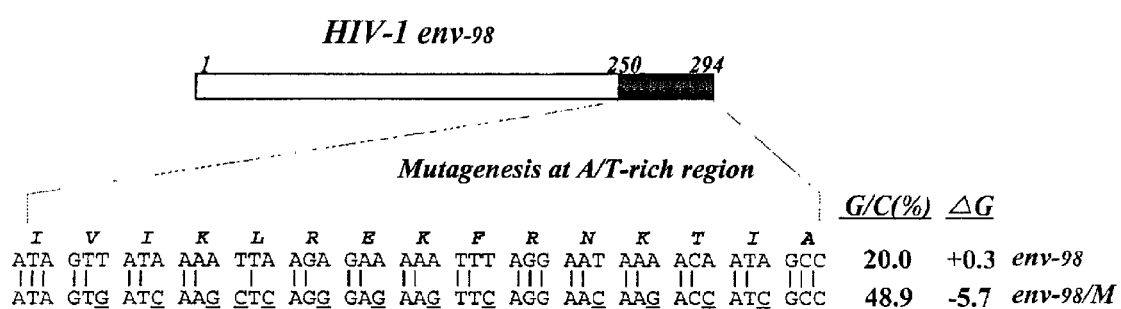
FIG. 7a illustrates the mutagenesis at A/T-rich region in HIV-1 env-98 according to G/C rule of this invention. The genetically unstable insert, HIV-1 env-98, was sequence-adjusted at the A/T-rich region marked by the solid box in the diagram. Thirteen A/T sites were substituted with G/C by mutagenesis without any change in the amino acid sequence.
Figure 7B:
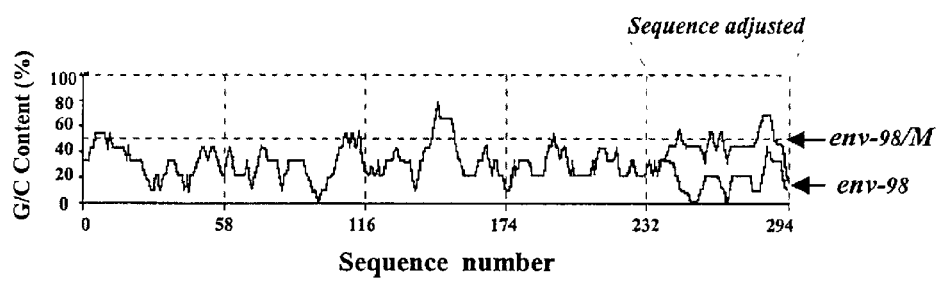
FIG. 7b is a histogram showing the G/C content of HIV-1 env-98 and HIV-1 env-98/M. The G/C contents of the inserts before and after sequence-substitution were analyzed by the DNASIS program at a window size 9, and were expressed by histogram. Sequence substitution increased the local G/C contents of the insert.
Figure 7C:
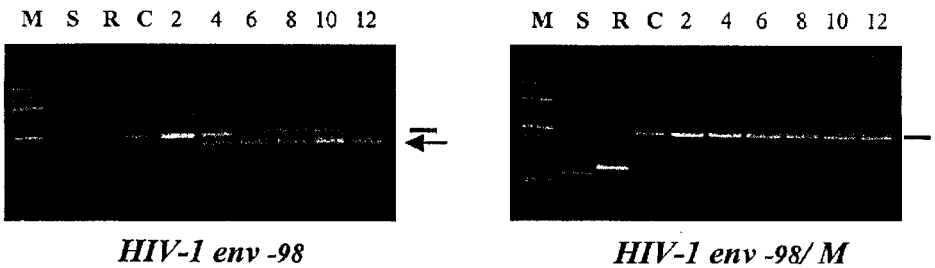
FIG. 7c is a photograph showing RT-PCR analysis demonstrating a genetic stability of HIV-1 env-98 or HIV-1 env-98/M integrated into RPS-Vax. M; 100 bp size marker, S; poliovirus Sabin 1, R; RPS-Vax vector-derived virus, C; insert-containing recombinant plasmid. The numbers represent the passage cycle of each rec-PV. The bar and arrow indicate the original and truncated bands of the insert, respectively.

To verify the hypothesis, multiple silent mutations were introduced into the A/T-rich region of the env-98 recombinant by replacing A/T with G/C at a total of 13 different positions around the 3' end, and measured the genetic stability of the mutant, called env-98/M (FIG. 7). These substitutions increased the regional G/C content up to 46.7% from 20% (FIGS. 7a and 7b). To our surprise, the HIV-1 env-98/M showed complete genetic stability throughout the passage (FIG. 7c). This result was also repeated in the HIV-1 env-71/M-integrated rec-PV (data not shown). These remarkable elevations of the rec-PV stability by sequence substitutions strongly suggest that the local A/T-rich sequence destabilizes the overall RNA structure and promotes the site-specific deletion of the neighboring region. It also demonstrates that the genetic stability can be manipulated by adjusting the global G/C content of the RNA insert.

Increasing the G/C Contents and Adjusting the G/C Distribution Patterns Dramatically Improved the Genetic Stability of the Rec-PV Containing Hetero-Multimeric Inserts In our experiments, the inventors found that the G/C contents and their distribution patterns are important for the genetic stability of foreign inserts less than 450 bp in the RPS-Vax-derived recombinant PV.

Figure 8:
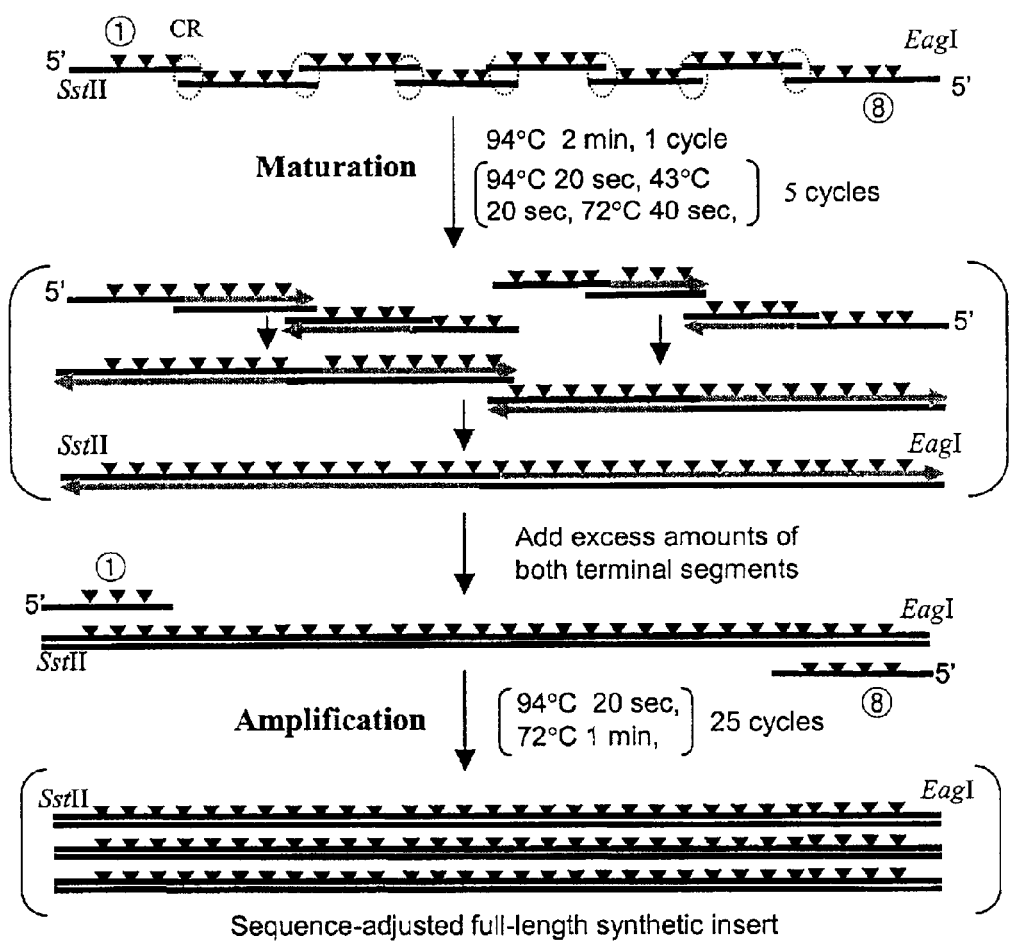
FIG. 8 illustrates one example of template/ligation-free PCR method of this invention. Schematic illustration for the template/ligation-free PCR procedures, which has been used for the synthesis of long hetero-multimeric concatamers or heavily sequence-adjusted inserts, without template DNA. CR means complementary region. The solid triangles represent the mutation sites on the synthetic DNA. The circled numbers 1 and 8 represent long synthetic primers of between 60 to 100 bases in length.
Figure 11:
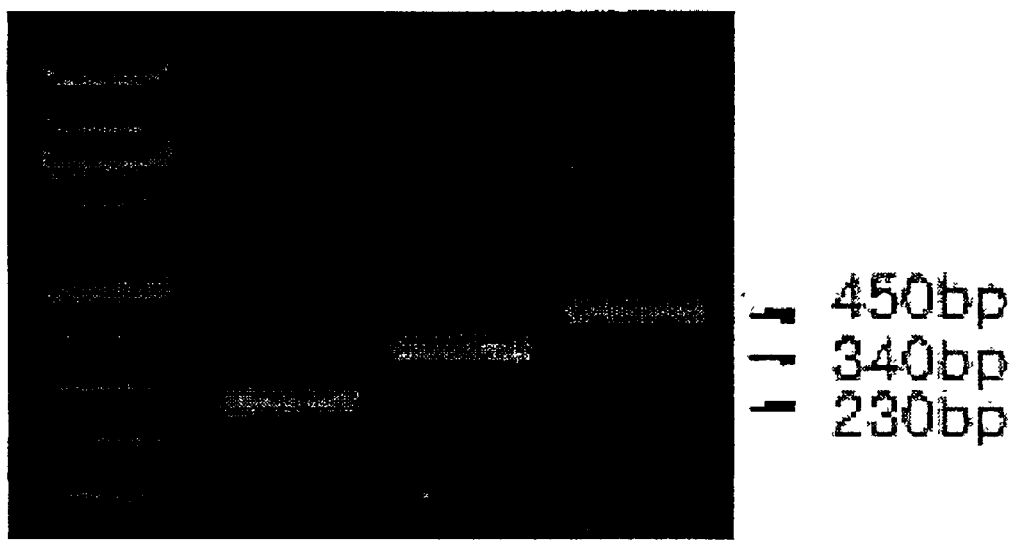
FIG. 11 is a photograph showing product from template/ligation-free PCR amplification of the nucleotide sequence encoding PVm-150/M. M; 100 bp size marker, 1; product using primers 1, 2, 3 and 4, 2; product using primers 1, 2, 3, 4, 5 and 6, 3; product using primers 1, 2, 3, 4, 5, 6, 7 and 8.

In order to verify our findings and to see whether they are applicable for generation of a genetically stable recombinant PV, the inventors have constructed three different heteromultimeric repeated inserts (PVm-150, PVm-137 and PVm-132) and their sequence-adjusted forms (PVm-150/M, PVm-137/M and PVm-132/M) by ligation-free PCR without a template, as described in the Materials and Methods and illustrated in FIG. 8. Sequence adjusting was performed without a change of amino acid sequences. Among these synthetic inserts, PVm-150 comprises 3 repeats of the VP1 neutralizing epitopes (12 amino acids) of poliovirus type 2 (Lancing), 2 repeats (10 amino acids) of poliovirus Type 3 (Leon), and 2 repeats of 5 amino acids (FIG. 9). PVm-150/M was synthesized by adjusting the sequence of PVm-150 on the basis of our G/C rules (FIG. 9). The sequence substitution increases the G/C contents and free energy of the PVm-150/M up to 58.4% and −138.9 Kcal, respectively (Table 1).

Figure 12A:
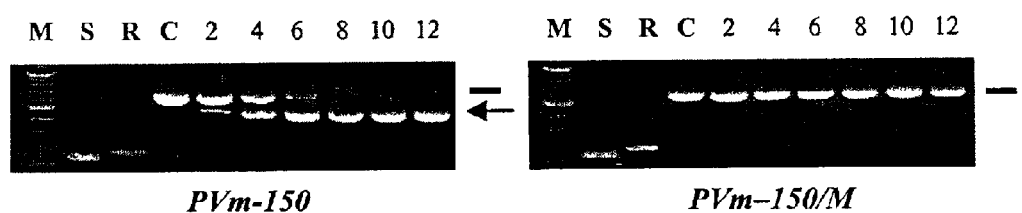
FIG. 12a is a photograph showing RT-PCR analysis demonstrating a genetic stability of the insert sequence, PVm-150/M integrated into RPS-Vax. M; 100 bp size marker, S; poliovirus Sabin 1, R; RPS-Vax vector-derived virus, C; insert-containing recombinant plasmid. The numbers represent the passage cycle of each rec-PV. The bar and arrow indicate the original and truncated bands of the insert, respectively.
Figure 12B:
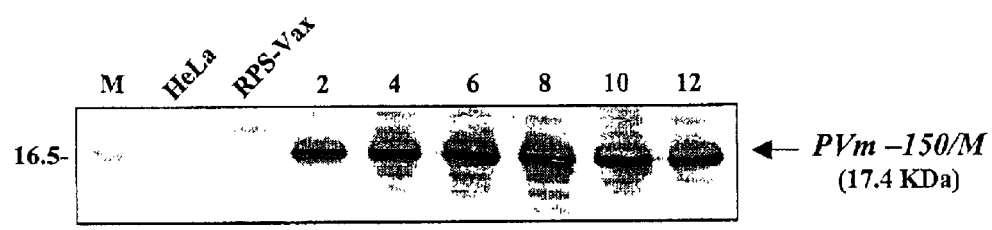
FIG. 12b is a photograph showing Western blot analysis demonstrating a protein stability of the insert sequence, PVm-150/M integrated into RPS-Vax. The numbers indicate the passage cycle of the rec-PV to be infected into HeLa cells. Uninfected, RPS-Vax-infected, and rec-PV-infected HeLa cell lysates were screened by Western blot with peptide-specific antiserum.

These synthetic genes were cloned into the RPS-Vax system, followed by production of rec-PVs. Rec-PV, RPS-Vax/PVm-150 was genetically unstable (left panel of FIG. 12a). On the contrary, its sequence-adjusted clone, the RPS-Vax/PVm-150/M, having high G/C contents and even G/C distribution without a change in the amino acid sequence, showed perfect genetic stability (right panel of FIG. 12a). The Rec-PV containing inserts, PVm-137 or PVm-132, were also genetically unstable, as shown by the RPS-Vax/PVm-150 (data not shown), but their sequence-adjusted constructs were quite stable during the consecutive passages (Table 1). Genetic stability of the RPS-Vax/PVm-150/M, examined by RT-PCR, was also confirmed by Western blot experiments (FIG. 12b). These results clearly demonstrate that our findings are applicable in explaining increases in the genetic stability of the RPS-Vax-derived rec-PVs even though they have repeated epitope-containing foreign inserts.

Recovered Genetic Stability of Rec-PV in HeLa Cell Culture was Also Maintained in vivo Up to now, the genetic stability of the rec-PV was examined by serial passages in the HeLa cell culture. To investigate whether the genetic stability of the rec-PV determined in cell cultures was also repeated in vivo, two recombinant viruses, RPS-Vax/PVm-150 and RPS-Vax/PVm-150/M, were respectively inoculated intracerebrally into Tg-PVR mice. The viruses were recovered daily from the spleen of each mouse for 4 days after the intracerebral injections, and tested for genetic stability using RT-PCR. As shown in FIG. 13, each recombinant virus recovered from the inoculated mice demonstrated very similar patterns of genetic stability to those shown in HeLa cell cultures. The RPS-Vax/PVm-150 showed serious internal deletion even in 2 days, and no intact bands longer 3 or more days after the inoculation (left panel in FIG. 13), suggesting that the rec-PVs having hetero-multimeric repeated sequences are very unstable during their replication, not only in vitro but also in vivo.

Whereas, the RPS-Vax/PVm-150/M, having sequences adjusted by our G/C rule without any amino acid changes in the insert, revealed complete genetic integrity without showing any insert deletion pattern during the same period of replication, even in vivo (right panel in FIG. 13). These results imply that the RPS-Vax-derived recombinant virus maintains its own genetic stability consistently during its replication, not only in vitro but also in vivo.

In the previous experiment with recombinant coxsackievirus B3 (Slifka, M. K. et al., 2001. Using recombinant coxsackievirus B3 to evaluate the induction and protective efficacy of CD8+T cells during picornavirus infection. *J. Virol.* 75:2377–2387), while the insert was retained through passage 4 in the tissue culture, it was almost lost in vivo in an organ-specific manner. Actually, the rec-PV showing genetic instability in a HeLa cell culture was much more unstable in infected mice (left panel in FIG. 13). Whereas, the sequence-adjusted rec-PV, RPS-Vax/PV23-150/M, showed complete genetic stability, even in vivo, during the same period (right panel in FIG. 13).

In conclusion, this invention demonstrates i) that the genetic stability of rec-PV is strongly associated with the G/C contents and G/C distribution patterns in foreign inserts, and ii) that the genetic instability of foreign inserts can be promoted by increasing the G/C contents and/or replacing the local A/T-rich region with the G/C-rich codon. Based on the present results, this inventors have established an insert-design architecture, which includes G/C rules and template/ligation-free PCR protocol. Our G/C rules are as follows: first, adopt a host-specific codon usage; second, use the high G/C-content codon from the available codons; third, distribute the G/C evenly; and fourth, minimize the local repeats throughout the whole insert.

The feasibility of our architectural design was confirmed by construction of a hetero-multimeric insert showing complete genetic stability, not only in vitro but also in vivo. These findings in this invention strongly suggest that the genetic stability of the rec-PV is closely related to the tertiary conformation of the insert RNA, which is determined mainly by its nucleotide composition. The suitability of the compact conformation of RNA in the encapsidation process, may account for its preference for the high G/C content and/or the even distribution of the G/C sequence for stable rec-PV. Even though these guidelines were established with a poliovirus-derived RPS-Vax vector system, to some extent, they would be applicable, not only for the construction of recombinant RNA viruses, but also for the development of other live vector-based vaccines.

Having described a preferred embodiment of the present invention, it is to be understood that variants and modifications thereof falling within the spirit of the invention may become apparent to those skilled in this art, and the scope of this invention is to be determined by appended claims and their equivalents.

TABLE 1

Genetic stability and other biochemical characteristics of RPS-Vax-derived recombinant-PV

| Foreign insert | Insert size [a] (bp) | HYD [b] | G/C content [c] (%) | ΔG [d] (kcal/mole) | Rec-Virus [e] (+/−) | Stable passage [f] (number) |
|---|---|---|---|---|---|---|
| Monomer | | | | | | |
| SIV gag-100 | 300 | −0.53 | 45.0 | −101.7 | + | >12 |
| SIV gag-100/M [¶] | 300 | −0.53 | 34.0 | −84.3 | + | 4 * |
| SIV gag-114 | 342 | −0.45 | 44.7 | −105.6 | + | >12 |
| SIV p27-167 | 501 | −0.55 | 43.7 | −92.6 | + | 5 [†] |
| SIV p27-150 | 450 | −0.48 | 43.8 | −102.3 | + | >12 |
| SIV env-108 | 294 | −0.89 | 35.4 | −82.8 | + | 5 * |

TABLE 1-continued

Genetic stability and other biochemical characteristics of RPS-Vax-derived recombinant-PV

| Foreign insert | Insert size [a] (bp) | HYD [b] | G/C content [c] (%) | ΔG [d] (kcal/mole) | Rec-Virus [e] (+/-) | Stable passage [f] (number) |
|---|---|---|---|---|---|---|
| SIV env-108/M [¶] | 294 | -0.89 | 50.3 | -112.7 | + | >12 |
| HIV-1 env-98 | 294 | -0.53 | 30.6 | -56.2 | + | 2 * |
| HI

```
<211> LENGTH: 300
<212> TYPE: DNA
<213> ORGANISM: Artificial Sequence
<220> FEATURE:
<223> OTHER INFORMATION: SIV gag-100/M

<400> SEQUENCE: 2
agtccaagaa cattaaatgc atgggtaaaa ttaatagaag aaaaaaaatt tggagcagaa      60
gtagttccag gatttcaagc attatcagaa ggttgtactc catatgatat taatcaaatg     120
ttaaattgtg taggagatca tcaagcagct atgcaaatta aagagatat  tataaatgaa     180 gaagctgcag attgggattt acaacatcca caaccagctc cacaacaagg acaattaaga     240
gaaccttcag gatcagatat tgcaggaaca actagttcag tagatgaaca aattcaatgg     300

<210> SEQ ID NO 3
<211> LENGTH: 342
<212> TYPE: DNA
<213> ORGANISM: Artificial Sequence
<220> FEATURE:
<223> OTHER INFORMATION: SIV gag-114

<400> SEQUENCE: 3
ccagtacaac aaataggtgg taactatgtc cacctgccat taagcccgag aacattaaat      60
gcctgggtaa aattgataga ggaaaagaaa tttggagcag aagtagtgcc aggatttcag     120
gcactgtcag aaggttgcac cccctatgac attaatcaga tgttaaattg tgtgggagac     180
catcaagcgg ctatgcagat tatcagagat attataaacg aggaggctgc agattgggac     240
ttgcagcacc cacaaccagc tccacaacaa ggacaactta gggagccgtc aggatcagat     300
attgcaggaa caactagttc agtagatgaa caaatccagt gg                       342

<210> SEQ ID NO 4
<211> LENGTH: 501
<212> TYPE: DNA
<213> ORGANISM: Artificial Sequence
<220> FEATURE:
<223> OTHER INFORMATION: SIV p27-167

<400> SEQUENCE: 4
ccagtacaac aaataggtgg taactatgtc cacctgccat taagcccgag aacattaaat      60
gcctgggtaa aattgataga ggaaaagaaa tttggagcag aagtagtgcc aggatttcag     120
gcactgtcag aaggttgcac cccctatgac attaatcaga tgttaaattg tgtgggagac     180
catcaagcgg ctatgcagat tatcagagat attataaacg aggaggctgc agattgggac     240
ttgcagcacc cacaaccagc tccacaacaa ggacaactta gggagccgtc aggatcagat     300
attgcaggaa caactagttc agtagatgaa caaatccagt ggatgtacag acaacagaac     360
cccataccag taggcaacat ttacaggaga tggatccaac tggggttgca aaaatgtgtc     420
agaatgtata acccaacaaa cattctagat gtaaaacaag gccaaaaga gccatttcag     480 agctatgtag acaggttcta c                                              501

<210> SEQ ID NO 5
<211> LENGTH: 450
<212> TYPE: DNA
<213> ORGANISM: Artificial Sequence
<220> FEATURE:
<223> OTHER INFORMATION: SIV p27-150

<400> SEQUENCE: 5
ccagtacaac aaataggtgg taactatgtc cacctgccat taagcccgag aacattaaat      60
```

```
gcctgggtaa aattgataga ggaaaagaaa tttggagcag aagtagtgcc aggatttcag      120
gcactgtcag aaggttgcac ccctatgac attaatcaga tgttaaattg tgtgggagac       180
catcaagcgg ctatgcagat tatcagagat attataaacg aggaggctgc agattgggac     240
ttgcagcacc cacaaccagc tccacaacaa ggacaactta gggagccgtc aggatcagat      300
attgcaggaa caactagttc agtagatgaa caaatccagt ggatgtacag acaacagaac      360
cccataccag taggcaacat ttacaggaga tggatccaac tggggttgca aaaatgtgtc      420
agaatgtata acccaacaaa cattctagat                                      450

<210> SEQ ID NO 6
<211> LENGTH: 324
<212> TYPE: DNA
<213> ORGANISM: Artificial Sequence
<220> FEATURE:
<223> OTHER INFORMATION: SIV env-108

<400> SEQUENCE: 6
acttctactt ggtttggctt taatggaact agagcagaaa atagaactta tatttactgg      60
catggtaggg ataataggac tataattagt ttaaataagt attataatct aacaatgaaa      120
tgtagaagac caggaaataa gacagtttta ccagtcacca ttatgtctgg attggttttc     180
cactcacaac caatcaatga taggccaaag caggcatggt gttggtttgg aggaaaatgg     240
aaggatgcaa taaagaggt gaagcagacc attgtcaaac atcccaggta tactggaact     300
aacaatactg ataaaatcaa tttg                                            324

<210> SEQ ID NO 7
<211> LENGTH: 324
<212> TYPE: DNA
<213> ORGANISM: Artificial Sequence
<220> FEATURE:
<223> OTHER INFORMATION: SIV env-108/M

<400> SEQUENCE: 7
actagcactt ggttcggctt caacggaact agggcagaga acagaactta catctactgg      60
catggtaggg acaaccggac gatcatcagc ctgaacaagt actacaacct caccatgaaa     120
tgcaggagac caggaaataa gacagtgcta ccagtcacca tcatgtccgg gttggtcttc     180
cactcacagc ccatcaatga caggcccaag caggcctggt gttggttcgg aggcaagtgg     240
aaggatgcca taaaggaggt gaagcagacc attgtcaagc atcccaggta cactggaact     300
aacaacactg acaagatcaa tttg                                            324

<210> SEQ ID NO 8
<211> LENGTH: 294
<212> TYPE: DNA
<213> ORGANISM: Artificial Sequence
<220> FEATURE:
<223> OTHER INFORMATION: HIV-1 env-98

<400> SEQUENCE: 8
ttaaatggca gtctagcaga agaagacata gtaattagat ctgaaaattt cacagacaat      60
gctaaaacca atatagtaca gctaaatgaa tctgtagtaa ttaattgtac aagacccaac     120
aacaatacaa gaagaaggtt atctatagga ccagggagag cattttatgc aagaagaaac     180
ataataggag atataagaca agcacattgt aacattagta gagcaaaatg gaataacact      240
ttacaacaga tagttataaa attaagagaa aaatttagga ataaaacaat agcc           294
```

<210> SEQ ID NO 9
<211> LENGTH: 294
<212> TYPE: DNA
<213> ORGANISM: Artificial Sequence
<220> FEATURE:
<223> OTHER INFORMATION: HIV-1 env-98/M

<400> SEQUENCE: 9

```
ttaaatggca gtctagcaga agaagacata gtaattagat ctgaaaattt cacagacaat      60
gctaaaacca taatagtaca gctaaatgaa tctgtagtaa ttaattgtac aagacccaac     120
aacaatacaa gaagaaggtt atctatagga ccagggagac cattttatgc aagaagaaac     180
ataataggag atataagaca agcacattgt aacattagta gagcaaaatg gaataacact     240
ttacaacaga tcgtgatcaa gcttcgggag aagttccgga acaagacgat cgcc          294
```

<210> SEQ ID NO 10
<211> LENGTH: 249
<212> TYPE: DNA
<213> ORGANISM: Artificial Sequence
<220> FEATURE:
<223> OTHER INFORMATION: HIV-1 env-83

<400> SEQUENCE: 10

```
ttaaatggca gtctagcaga agaagacata gtaattagat ctgaaaattt cacagacaat      60
gctaaaacca taatagtaca gctaaatgaa tctgtagtaa ttaattgtac aagacccaac     120
aacaatacaa gaagaaggtt atctatagga ccagggagac cattttatgc aagaagaaac     180
ataataggag atataagaca agcacattgt aacattagta gagcaaaatg gaataacact     240
ttacaacag                                                             249
```

<210> SEQ ID NO 11
<211> LENGTH: 213
<212> TYPE: DNA
<213> ORGANISM: Artificial Sequence
<220> FEATURE:
<223> OTHER INFORMATION: HIV-1 env-71

<400> SEQUENCE: 11

```
ctaaatgaat ctgtagtaat taattgtaca agacccaaca acaatacaag aagaaggtta      60
tctataggac cagggagagc atttatgca agaagaaaca taataggaga tataagacaa     120
gcacattgta acattagtag agcaaaatgg aataacactt tacaacagat agttataaaa     180
ttaagagaaa aatttaggaa taaaacaata gcc                                  213
```

<210> SEQ ID NO 12
<211> LENGTH: 381
<212> TYPE: DNA
<213> ORGANISM: Artificial Sequence
<220> FEATURE:
<223> OTHER INFORMATION: PV 2-127

<400> SEQUENCE: 12

```
gcgctgacag ccgtagagac aggggccacc aacccattgg tgccttcaga cacggtacaa      60
actcgtcacg tcatccaaaa gcggacgcgg tcggagtcta cggttgagtc tttcttcgca     120
agaggagctt gtgtggccat tattgaagtg ataatgatg ctccaacaag gcgtgccagt     180
aaattatttt cagtctggaa gataacttac aaggacaccg ttcagttaag acgtaagttg     240
gagttcttta catattcaag gtttgacatg gagttcacct ttgtggttac atccaattat     300
accgatgcaa acaatgggca cgcactgaat caagtttacc agataatgta cataccacct     360
```

```
ggggcaccga tccctggcaa g                                           381

<210> SEQ ID NO 13
<211> LENGTH: 354
<212> TYPE: DNA
<213> ORGANISM: Artificial Sequence
<220> FEATURE:
<223> OTHER INFORMATION: PV 2-118

<400> SEQUENCE: 13
gcttgtgtgg ccattattga agtggataat gatgctccaa caaggcgtgc cagtaaatta    60
ttttcagtct ggaagataac ttacaaggac accgttcagt taagacgtaa gttggagttc   120
tttacatatt caaggtttga catggagttc acctttgtgg ttacatccaa ttataccgat   180
gcaaacaatg ggcacgcact gaatcaagtt taccagataa tgtacatacc acctggggca   240
ccgatccctg gcaagcggaa tgattacaca tggcaaacgt catctaaccc atcagtgttt   300
tacacttacg gggcacctcc agctagaata tcagtgccct acgtgggcat tgcc         354

<210> SEQ ID NO 14
<211> LENGTH: 330
<212> TYPE: DNA
<213> ORGANISM: Artificial Sequence
<220> FEATURE:
<223> OTHER INFORMATION: PV 3-110

<400> SEQUENCE: 14
cacgtagtcc aacgacgcag caggtcagag tccacaatag aatcattctt cgcacgcggg    60
gcgtgcgtcg ctattattga ggtggacaat gaacaaccaa ccacccgggc acagaaacta   120
tttgccatgt ggcgcattac atacaaagat acagtgcagt tgcgccgtaa gttggagttt   180
ttcacatact ctcgttttga catggaattc accttcgtgg taaccgccaa cttcaccaac   240
gctaataatg ggcatgcact caaccaggtg taccagataa tgtacatccc cccaggggca   300
cccacaccaa agtcatggga cgactacact                                     330

<210> SEQ ID NO 15
<211> LENGTH: 480
<212> TYPE: DNA
<213> ORGANISM: Artificial Sequence
<220> FEATURE:
<223> OTHER INFORMATION: HCV core-160

<400> SEQUENCE: 15
atgagcacaa atcctaaacc tcaaagaaaa accaaaagaa acaccaaccg tcgcccacaa    60
gacgtcaagt tcccgggcgg tggtcagatc gttggtggag tttacctgtt gccgcgcagg   120
ggccccaggt tgggtgtgcg cgcgactagg aagacttccg agcggtcgca acctcgtgga   180
aggcgacagc ctatcccaa ggctcgccaa cccgagggta ggacctgggc tcagcccggg   240 taccccttggc ccctctatgg caatgagggt ctgggatggg caggatggct cctgtcaccc   300
cgcggctctc ggcctagttg ggccccaca gaccccggc gtaggtcgcg taatttgggt   360
aaggtcatcg atactctcac atgcggcttc gccgacctca tgggtacat tccgctcgtc   420 ggcgcccccc taggggggcgt tgccagggcc ttggcacatg gtgtccggct tctggaggac   480

<210> SEQ ID NO 16
<211> LENGTH: 300
<212> TYPE: DNA
<213> ORGANISM: Artificial Sequence
<220> FEATURE:
```

<223> OTHER INFORMATION: HCV core-100

<400> SEQUENCE: 16

```
atgagcacaa atcctaaacc tcaaagaaaa accaaaagaa acaccaaccg tcgcccacaa      60
gacgtcaagt tcccgggcgg tggtcagatc gttggtggag tttacctgtt gccgcgcagg     120
ggccccaggt tgggtgtgcg cgcgactagg aagacttccg agcggtcgca acctcgtgga    180
aggcgacagc ctatcccaa ggctcgccaa cccgagggta ggacctgggc tcagcccggg     240
tacccttggc ccctctatgg caatgagggt ctgggatggg caggatggct cctgtcaccc    300
```

<210> SEQ ID NO 17
<211> LENGTH: 399
<212> TYPE: DNA
<213> ORGANISM: Artificial Sequence
<220> FEATURE:
<223> OTHER INFORMATION: PV 2.3-131

<400> SEQUENCE: 17

```
gcgctgacag ccgtagagac aggggccacc aacccattgg tgccttcaga cacggtacaa     60
actcgtcacg tcatccaaaa gcggacgcgg tcggagtcta cggttgagtc tttcttcgca    120
agaggagctt gtgtggccat tattgaagtg ataatgatg ctccaacaag gcgtgccagt    180
aaattatttt cagtctggaa gataaactgaa ttcgagtcca caatagaatc attcttcgca    240
cgcggggcgt gcgtcgctat tattgaggtg gacaatgaac aaccaaccac ccgggcacag    300
aaactatttg ccatgtggcg cattacatac aaagatacag tgcagttgcg ccgtaagttg    360
gagttttca catactctcg ttttgacatg gaattcacc                              399
```

<210> SEQ ID NO 18
<211> LENGTH: 336
<212> TYPE: DNA
<213> ORGANISM: Artificial Sequence
<220> FEATURE:
<223> OTHER INFORMATION: PV 2.3-112

<400> SEQUENCE: 18

```
gcttgtgtgg ccattattga agtggataat gatgctccaa caaggcgtgc cagtaaatta     60
ttttcagtct ggaagataac ttacaaggac accgttcagt taagacgtaa gttggagttc    120
tttacatatt caaggtttga catggagttc acctttgtgg ttacaggatc cgcgtgcgtc    180
gctattattg aggtggacaa tgaacaacca ccaccgggg cacagaaact atttgccatg    240
tggcgcatta catacaaaga tacagtgcag ttgcgccgta agttggagtt tttcacatac    300
tctcgttttg acatggaatt caccttcgtg gtaacc                               336
```

<210> SEQ ID NO 19
<211> LENGTH: 306
<212> TYPE: DNA
<213> ORGANISM: Artificial Sequence
<220> FEATURE:
<223> OTHER INFORMATION: HBVcs

<400> SEQUENCE: 19

```
ttgtggtttc acatttcctg tcttacgttt gggagacaaa ctgttcttga atatttggtg     60
tcctttggag tgtggattcg cactcctcct gcatatagac accaaatgc cctatctta    120
tcaacacttc cggaaactac tgttgttaga gaattcccag gatcatcaac caccagcacg    180
ggaccatgca agacttgcac agctcctgct caaggaacct ctatgtttcc ctcatgttgc    240
tgtacaaaac ctacggacgg aaactgcacc tgtattccca tcccatcatc ttgggctttc    300
```

```
gcaaaa                                                          306

<210> SEQ ID NO 20
<211> LENGTH: 360
<212> TYPE: DNA
<213> ORGANISM: Artificial Sequence
<220> FEATURE:
<223> OTHER INFORMATION: HIV-1 mV3

<400> SEQUENCE: 20
attaattgta caagacccaa caacaataca agaagaaggt tatctatagg accagggaga    60
gcattttatg caagaagaaa cataatagga gatataagac aagcacattg taacattgaa   120
ttcattaatt gtacaagacc caacaacaat acaagaagaa ggttatctat aggaccaggg   180
agagcatttt atgcaagaag aaacataata ggagatataa gacaagcaca ttgtaacatt   240
ctgcagatta attgtacaag acccaacaac aatacaagaa gaaggttatc tataggacca   300
gggagagcat tttatgcaag aagaaacata ataggagata taagacaagc acattgtaac   360

<210> SEQ ID NO 21
<211> LENGTH: 240
<212> TYPE: DNA
<213> ORGANISM: Artificial Sequence
<220> FEATURE:
<223> OTHER INFORMATION: HIV-1 PND8

<400> SEQUENCE: 21
tctataggac cagggagagc attttatgca tctataggac cagggagagc attttatgca    60
tctataggac cagggagagc attttatgca tctataggac cagggagagc attttatgca   120
tctataggac cagggagagc attttatgca tctataggac cagggagagc attttatgca   180
tctataggac cagggagagc attttatgca tctataggac cagggagagc attttatgca   240

<210> SEQ ID NO 22
<211> LENGTH: 450
<212> TYPE: DNA
<213> ORGANISM: Artificial Sequence
<220> FEATURE:
<223> OTHER INFORMATION: PVm-150/M

<400> SEQUENCE: 22
gctaaggccg ttgcagcctg gaccctgaaa gccgctgcag gccaagcctc caccgaaggc    60
gactgcggtt gcccagccat catcgaggtc gataacgatg cccctaccaa gcgagccagc   120
aagctcttca gcgaattcga ggtcgataat gagcagccca ctacccgagc ccagaagctc   180
ttcgccatgt ggcgtatcac ttacaaggac aatgatgcgc caactaagcg cgcatctaaa   240
ctgtgcgtcc gaatctacat gaagcccaag cacgttcgat gctccggctg tcccgctatt   300
atcgaagtgg ataacgacgc accaaccaaa cgggcatcaa agctggacaa ctaccagtcc   360
ccatgcgcga tcaacgagca acctaccacc cgtgcgcaaa agtccgctgg gtgcttctat   420
cagacccgcg tcgtggttcc ctcaggttgt                                    450

<210> SEQ ID NO 23
<211> LENGTH: 411
<212> TYPE: DNA
<213> ORGANISM: Artificial Sequence
<220> FEATURE:
<223> OTHER INFORMATION: PVm-137/M

<400> SEQUENCE: 23
```

```
ttctaccaga cgcgagtggt tgtcccagac aacgaacagc cgactacccg ggcaggccaa      60
gcctccaccg aaggcgactg cggttgccca gccatcatcg aggtcgataa tgagcagccc     120
actacccgag cccagaagct cttcgccatg tggcgtatca cttacaagga caatgatgcg     180
ccaactaagc gcgcatctaa actgtgcgtc cgaatctaca tgaagcccaa gcacgttcga     240
tgctccggct gtcccgctat tatcgaagtg gataacgacg caccaaccaa acgggcatca     300
aagctggaca actaccagtc cccatgcgcg atcaacgagc aacctaccac ccgtgcgcaa     360
aagtccgctg ggtgcttcta tcagacccgc gtcgtggttc cctcaggttg t              411

<210> SEQ ID NO 24
<211> LENGTH: 396
<212> TYPE: DNA
<213> ORGANISM: Artificial Sequence
<220> FEATURE:
<223> OTHER INFORMATION: PVm-132/M

<400> SEQUENCE: 24
gctaaggccg ttgcagcctg gaccctgaaa gccgctgcag gccaagcctc caccgaaggc      60
gactgcggtt gccagccat catcgaggtc gataatgagc agcccactac ccgagcccag     120
aagctcttcg ccatgtggcg tatcacttac aaggacaatg atgcgccaac taagcgcgca     180
tctaaactgt gcgtccgaat ctacatgaag cccaagcacg ttcgatgctc cggctgtccc     240
gctattatcg aagtggataa cgacgcacca accaaacggg catcaaagct ggacaactac     300
cagtccccat gcgcgatcaa cgagcaacct accaccccgtg cgcaaaagtc cgctgggtgc     360
ttctatcaga cccgcgtcgt ggttccctca ggttgt                              396

<210> SEQ ID NO 25
<211> LENGTH: 31
<212> TYPE: DNA
<213> ORGANISM: Artificial Sequence
<220> FEATURE:
<223> OTHER INFORMATION: sense primer for PCR amplification of SIV
      gag-100

<400> SEQUENCE: 25
attataccgc ggagcccgag aacattaaat g                                    31

<210> SEQ ID NO 26
<211> LENGTH: 31
<212> TYPE: DNA
<213> ORGANISM: Artificial Sequence
<220> FEATURE:
<223> OTHER INFORMATION: antisense primer for PCR amplification of SIV
      gag-100

<400> SEQUENCE: 26
attattgccg gcccactgga tttgttcatc t                                    31

<210> SEQ ID NO 27
<211> LENGTH: 32
<212> TYPE: DNA
<213> ORGANISM: Artificial Sequence
<220> FEATURE:
<223> OTHER INFORMATION: sense primer for PCR amplification of SIV
      gag-114

<400> SEQUENCE: 27
ttaattccgc ggccagtaca acaaataggt gg                                   32

<210> SEQ ID NO 28
```

```
<211> LENGTH: 33
<212> TYPE: DNA
<213> ORGANISM: Artificial Sequence
<220> FEATURE:
<223> OTHER INFORMATION: antisense primer for PCR amplification of SIV
      gag-114

<400> SEQUENCE: 28
aatatagccg gcccactgga tttgttcatc tac                            33

<210> SEQ ID NO 29
<211> LENGTH: 31
<212> TYPE: DNA
<213> ORGANISM: Artificial Sequence
<220> FEATURE:
<223> OTHER INFORMATION: sense primer for PCR amplification of SIV
      p27-167

<400> SEQUENCE: 29
atattaccgc ggccagtaca acaaataggt g                              31

<210> SEQ ID NO 30
<211> LENGTH: 33
<212> TYPE: DNA
<213> ORGANISM: Artificial Sequence
<220> FEATURE:
<223> OTHER INFORMATION: antisense primer for PCR amplification of SIV
      p27-167

<400> SEQUENCE: 30
ttaattgccg gcgtagaacc tgtctacata gct                            33

<210> SEQ ID NO 31
<211> LENGTH: 32
<212> TYPE: DNA
<213> ORGANISM: Artificial Sequence
<220> FEATURE:
<223> OTHER INFORMATION: sense primer for PCR amplification of SIV
      p27-150

<400> SEQUENCE: 31
tataatccgc ggccagtaca acaaataggt gg                             32

<210> SEQ ID NO 32
<211> LENGTH: 34
<212> TYPE: DNA
<213> ORGANISM: Artificial Sequence
<220> FEATURE:
<223> OTHER INFORMATION: antisense primer for PCR amplification of SIV
      p27-150

<400> SEQUENCE: 32
aatattgccg gcatctagaa tgtttgttgg gtta                           34

<210> SEQ ID NO 33
<211> LENGTH: 32
<212> TYPE: DNA
<213> ORGANISM: Artificial Sequence
<220> FEATURE:
<223> OTHER INFORMATION: sense primer for PCR amplification of SIV
      env-108

<400> SEQUENCE: 33
ttaaatccgc ggacttctac ttggtttggc tt                             32

<210> SEQ ID NO 34
<211> LENGTH: 34
```

```
<212> TYPE: DNA
<213> ORGANISM: Artificial Sequence
<220> FEATURE:
<223> OTHER INFORMATION: antisense primer for PCR amplification of SIV
      env-108/M

<400> SEQUENCE: 34
tatattgccg gccaaattga ttttatcagt attg                              34

<210> SEQ ID NO 35
<211> LENGTH: 35
<212> TYPE: DNA
<213> ORGANISM: Artificial Sequence
<220> FEATURE:
<223> OTHER INFORMATION: sense primer for PCR amplification of HIV-1
      env-98

<400> SEQUENCE: 35
ataataccgc ggttaaatgg cagtctagca gaaga                             35

<210> SEQ ID NO 36
<211> LENGTH: 39
<212> TYPE: DNA
<213> ORGANISM: Artificial Sequence
<220> FEATURE:
<223> OTHER INFORMATION: antisense primer for PCR amplification of HIV-1
      env-98

<400> SEQUENCE: 36
ataaatgccg gcggctattg ttttattcct aaattttc                          39

<210> SEQ ID NO 37
<211> LENGTH: 32
<212> TYPE: DNA
<213> ORGANISM: Artificial Sequence
<220> FEATURE:
<223> OTHER INFORMATION: sense primer for PCR amplification of HIV-1
      env-83

<400> SEQUENCE: 37
taaataccgc ggttaaatgg cagtctagca ga                                32

<210> SEQ ID NO 38
<211> LENGTH: 33
<212> TYPE: DNA
<213> ORGANISM: Artificial Sequence
<220> FEATURE:
<223> OTHER INFORMATION: antisense primer for PCR amplification of HIV-1
      env-83

<400> SEQUENCE: 38
attattgccg gcctgttgta aagtgttatt cca                               33

<210> SEQ ID NO 39
<211> LENGTH: 34
<212> TYPE: DNA
<213> ORGANISM: Artificial Sequence
<220> FEATURE:
<223> OTHER INFORMATION: sense primer for PCR amplification of HIV-1
      env-71

<400> SEQUENCE: 39
aatataccgc ggctaaatga atctgtagta atta                              34

<210> SEQ ID NO 40
<211> LENGTH: 35
<212> TYPE: DNA
```

```
<213> ORGANISM: Artificial Sequence
<220> FEATURE:
<223> OTHER INFORMATION: antisense primer for PCR amplification of HIV-1
      env-71

<400> SEQUENCE: 40
ataatagccg gcggctattg ttttattcct aaatt                          35

<210> SEQ ID NO 41
<211> LENGTH: 34
<212> TYPE: DNA
<213> ORGANISM: Artificial Sequence
<220> FEATURE:
<223> OTHER INFORMATION: sense primer for PCR amplification of HIV-1
      env-98/M

<400> SEQUENCE: 41
agttcaggaa caagaccatc gcccggccgt atta                           34

<210> SEQ ID NO 42
<211> LENGTH: 35
<212> TYPE: DNA
<213> ORGANISM: Artificial Sequence
<220> FEATURE:
<223> OTHER INFORMATION: antisense primer for PCR amplification of HIV-1
      env-98/M

<400> SEQUENCE: 42
tctccctaag cttgatcact atctgttgta aagtg                          35

<210> SEQ ID NO 43
<211> LENGTH: 30
<212> TYPE: DNA
<213> ORGANISM: Artificial Sequence
<220> FEATURE:
<223> OTHER INFORMATION: sense primer for PCR amplification of PV 2-127

<400> SEQUENCE: 43
aatttaccgc gggcgctgac agccgtagag                                30

<210> SEQ ID NO 44
<211> LENGTH: 30
<212> TYPE: DNA
<213> ORGANISM: Artificial Sequence
<220> FEATURE:
<223> OTHER INFORMATION: antisense primer for PCR amplification of
      PV 2-127

<400> SEQUENCE: 44
ttaatagccg gccttgccag ggatcggtgc                                30

<210> SEQ ID NO 45
<211> LENGTH: 31
<212> TYPE: DNA
<213> ORGANISM: Artificial Sequence
<220> FEATURE:
<223> OTHER INFORMATION: sense primer for PCR amplification of PV 2-118

<400> SEQUENCE: 45
attataccgc gggcttgtgt ggccattatt g                              31

<210> SEQ ID NO 46
<211> LENGTH: 30
<212> TYPE: DNA
<213> ORGANISM: Artificial Sequence
<220> FEATURE:
<223> OTHER INFORMATION: antisense primer for PCR amplification of
```

```
        PV 2-118

<400> SEQUENCE: 46
ataatagccg gcggcaatgc ccacgtaggg                                30

<210> SEQ ID NO 47
<211> LENGTH: 30
<212> TYPE: DNA
<213> ORGANISM: Artificial Sequence
<220> FEATURE:
<223> OTHER INFORMATION: sense primer for PCR amplification of PV 3-110

<400> SEQUENCE: 47
ataataccgc ggcacgtagt ccaacgacgc                                30

<210> SEQ ID NO 48
<211> LENGTH: 30
<212> TYPE: DNA
<213> ORGANISM: Artificial Sequence
<220> FEATURE:
<223> OTHER INFORMATION: antisense primer for PCR amplification of
        PV 3-110

<400> SEQUENCE: 48
aataatgccg gcagtgtagt cgtcccatga                                30

<210> SEQ ID NO 49
<211> LENGTH: 32
<212> TYPE: DNA
<213> ORGANISM: Artificial Sequence
<220> FEATURE:
<223> OTHER INFORMATION: sense primer for PCR amplification of HCV
        core-160

<400> SEQUENCE: 49
ataataccgc ggatgagcac aaatcctaaa cc                             32

<210> SEQ ID NO 50
<211> LENGTH: 32
<212> TYPE: DNA
<213> ORGANISM: Artificial Sequence
<220> FEATURE:
<223> OTHER INFORMATION: antisense primer for PCR amplification of HCV
        core-160

<400> SEQUENCE: 50
ttaattgccg gcgtcctcca gaagccggac ac                             32

<210> SEQ ID NO 51
<211> LENGTH: 36
<212> TYPE: DNA
<213> ORGANISM: Artificial Sequence
<220> FEATURE:
<223> OTHER INFORMATION: sense primer for PCR amplification of HCV
        core-100

<400> SEQUENCE: 51
aatataccgc ggatgagcac aaatcctaaa cctcaa                         36

<210> SEQ ID NO 52
<211> LENGTH: 31
<212> TYPE: DNA
<213> ORGANISM: Artificial Sequence
<220> FEATURE:
<223> OTHER INFORMATION: antisense primer for PCR amplification of HCV
        core-100
```

<400> SEQUENCE: 52
atatttgccg gcgggtgaca ggagccatcc t                                    31

<210> SEQ ID NO 53
<211> LENGTH: 32
<212> TYPE: DNA
<213> ORGANISM: Artificial Sequence
<220> FEATURE:
<223> OTHER INFORMATION: sense primer for PCR amplification of HBVsAg
      -100

<400> SEQUENCE: 53
atatatccgc ggcttctgga ctatcaaggt at                                   32

<210> SEQ ID NO 54
<211> LENGTH: 32
<212> TYPE: DNA
<213> ORGANISM: Artificial Sequence
<220> FEATURE:
<223> OTHER INFORMATION: antisense primer for PCR amplification of
      HBVsAg-100

<400> SEQUENCE: 54
ataaatgccg gcccatataa ctgaaagcca ga                                   32

<210> SEQ ID NO 55
<211> LENGTH: 30
<212> TYPE: DNA
<213> ORGANISM: Artificial Sequence
<220> FEATURE:
<223> OTHER INFORMATION: sense primer for PCR amplification of HBVsAg-76

<400> SEQUENCE: 55
attattccgc ggatggagag catcgcatca                                      30

<210> SEQ ID NO 56
<211> LENGTH: 30
<212> TYPE: DNA
<213> ORGANISM: Artificial Sequence
<220> FEATURE:
<223> OTHER INFORMATION: antisense primer for PCR amplification of
      HBVsAg-76

<400> SEQUENCE: 56
ataatagccg gcacacatcc agcgataacc                                      30

<210> SEQ ID NO 57
<211> LENGTH: 27
<212> TYPE: DNA
<213> ORGANISM: Artificial Sequence
<220> FEATURE:
<223> OTHER INFORMATION: sense primer(Sst II/ W2: 2608-2623) for PCR
      amplification of PV2,3-131

<400> SEQUENCE: 57
attaatccgc gggcgctgac agccgta                                         27

<210> SEQ ID NO 58
<211> LENGTH: 30
<212> TYPE: DNA
<213> ORGANISM: Artificial Sequence
<220> FEATURE:
<223> OTHER INFORMATION: antisense primer(EcoR I/W2: 2800-2814) for PCR
      amplification of PV2,3-131

<400> SEQUENCE: 58

```
atattagaat tcagttatct tccagactga                                    30
```

<210> SEQ ID NO 59
<211> LENGTH: 30
<212> TYPE: DNA
<213> ORGANISM: Artificial Sequence
<220> FEATURE:
<223> OTHER INFORMATION: sense primer(EcoR I/Leon: 2690-2707) for PCR amplification of PV2,3-131

<400> SEQUENCE: 59

```
attatcgaat tcgagtccac aatagaatca                                    30
```

<210> SEQ ID NO 60
<211> LENGTH: 30
<212> TYPE: DNA
<213> ORGANISM: Artificial Sequence
<220> FEATURE:
<223> OTHER INFORMATION: antisense primer(Eag I/Leon: 2958-2975) for PCR amplification of PV2,3-131

<400> SEQUENCE: 60

```
attaatcggc cgttccatgt caaaacgaga                                    30
```

<210> SEQ ID NO 61
<211> LENGTH: 29
<212> TYPE: DNA
<213> ORGANISM: Artificial Sequence
<220> FEATURE:
<223> OTHER INFORMATION: sense primer(Sst II/W2 VP1: 253-269) for PCR amplification of PV2,3-112

<400> SEQUENCE: 61

```
attaatccgc gggcttgtgt ggccattat                                     29
```

<210> SEQ ID NO 62
<211> LENGTH: 30
<212> TYPE: DNA
<213> ORGANISM: Artificial Sequence
<220> FEATURE:
<223> OTHER INFORMATION: antisense primer(BamH I/W2 VP1: 417-400) for PCR amplification of PV2,3-112

<400> SEQUENCE: 62

```
atattaggat cctgtaacca caaaggtgaa                                    30
```

<210> SEQ ID NO 63
<211> LENGTH: 27
<212> TYPE: DNA
<213> ORGANISM: Artificial Sequence
<220> FEATURE:
<223> OTHER INFORMATION: sense primer(BamH I/Leon VP1: 274-261) for PCR amplification of PV2,3-112

<400> SEQUENCE: 63

```
attatcggat ccgcgtgcgt cgctatt                                       27
```

<210> SEQ ID NO 64
<211> LENGTH: 28
<212> TYPE: DNA
<213> ORGANISM: Artificial Sequence
<220> FEATURE:
<223> OTHER INFORMATION: antisense primer(Eag I/Leon VP1: 411-396) for PCR amplification of PV2,3-112

<400> SEQUENCE: 64

```
attaatcggc cgggttacca cgaaggtg                                      28
```

<210> SEQ ID NO 65
<211> LENGTH: 30
<212> TYPE: DNA
<213> ORGANISM: Artificial Sequence
<220> FEATURE:
<223> OTHER INFORMATION: sense primer(core-Sst II) for PCR amplification of HBVcs

<400> SEQUENCE: 65
aatataccgc ggttgtggtt tccatttcct                                        30

<210> SEQ ID NO 66
<211> LENGTH: 29
<212> TYPE: DNA
<213> ORGANISM: Artificial Sequence
<220> FEATURE:
<223> OTHER INFORMATION: antisense primer(core-Hind III) for PCR amplification of HBVcs

<400> SEQUENCE: 66
cctgggaatt ctctaacaac agtagtttc                                         29

<210> SEQ ID NO 67
<211> LENGTH: 30
<212> TYPE: DNA
<213> ORGANISM: Artificial Sequence
<220> FEATURE:
<223> OTHER INFORMATION: sense primer(surface-Hind III) for PCR amplification of HBVcs

<400> SEQUENCE: 67
atatatgaat tcccaggatc atcaaccacc                                        30

<210> SEQ ID NO 68
<211> LENGTH: 33
<212> TYPE: DNA
<213> ORGANISM: Artificial Sequence
<220> FEATURE:
<223> OTHER INFORMATION: antisense primer(surface-Eag I) for PCR amplification of HBVcs

<400> SEQUENCE: 68
ataatagccg gcttttgcga aagcccaaga tga                                    33

<210> SEQ ID NO 69
<211> LENGTH: 30
<212> TYPE: DNA
<213> ORGANISM: Artificial Sequence
<220> FEATURE:
<223> OTHER INFORMATION: sense primer(BamH I-V3) for PCR amplification of HIV-1 mV3

<400> SEQUENCE: 69
acccgggatc cactgctgtt aaatggcagt                                        30

<210> SEQ ID NO 70
<211> LENGTH: 28
<212> TYPE: DNA
<213> ORGANISM: Artificial Sequence
<220> FEATURE:
<223> OTHER INFORMATION: antisense primer(EcoR I-V3) for PCR amplification of HIV-1 mV3

<400> SEQUENCE: 70
ctacagaatt caatgttaca atgtgctt                                          28

```
<210> SEQ ID NO 71
<211> LENGTH: 28
<212> TYPE: DNA
<213> ORGANISM: Artificial Sequence
<220> FEATURE:
<223> OTHER INFORMATION: sense primer(EcoR I-V3) for PCR amplification
      of HIV-1 mV3

<400> SEQUENCE: 71
ctacagaatt cattaattgt acaagacc                                          28

<210> SEQ ID NO 72
<211> LENGTH: 28
<212> TYPE: DNA
<213> ORGANISM: Artificial Sequence
<220> FEATURE:
<223> OTHER INFORMATION: antisense primer(V3-PstI) for PCR
      amplification of HIV-1 mV3

<400> SEQUENCE: 72
caagtctgca gaatgttaca atgtgctt                                          28

<210> SEQ ID NO 73
<211> LENGTH: 28
<212> TYPE: DNA
<213> ORGANISM: Artificial Sequence
<220> FEATURE:
<223> OTHER INFORMATION: sense primer(PstI-V3) for PCR amplification of
      HIV-1 mV3

<400> SEQUENCE: 73
caagtctgca gattaattgt acaagacc                                          28

<210> SEQ ID NO 74
<211> LENGTH: 32
<212> TYPE: DNA
<213> ORGANISM: Artificial Sequence
<220> FEATURE:
<223> OTHER INFORMATION: antisense primer(V3-Hind III) for PCR
      amplification of HIV-1 mV3

<400> SEQUENCE: 74
gcattaagct taaatgttac aatgtgcttg tc                                     32

<210> SEQ ID NO 75
<211> LENGTH: 29
<212> TYPE: DNA
<213> ORGANISM: Artificial Sequence
<220> FEATURE:
<223> OTHER INFORMATION: sense primer(SstII-V3) for PCR amplification
      of HIV-1 mV3

<400> SEQUENCE: 75
aggcctccgc ggattaattg tacaagacc                                         29

<210> SEQ ID NO 76
<211> LENGTH: 29
<212> TYPE: DNA
<213> ORGANISM: Artificial Sequence
<220> FEATURE:
<223> OTHER INFORMATION: antisense primer(V3-EagI) for PCR
      amplification of HIV-1 mV3

<400> SEQUENCE: 76
aggcctcggc cgaatgttac aatgtgctt                                         29
```

<210> SEQ ID NO 77
<211> LENGTH: 30
<212> TYPE: DNA
<213> ORGANISM: Artificial Sequence
<220> FEATURE:
<223> OTHER INFORMATION: sense primer(PND) for PCR amplification of
      HIV-1 PND8

<400> SEQUENCE: 77
cagaggggac cagggagagc atttgttaca                                    30

<210> SEQ ID NO 78
<211> LENGTH: 30
<212> TYPE: DNA
<213> ORGANISM: Artificial Sequence
<220> FEATURE:
<223> OTHER INFORMATION: antisense primer(PND) for PCR amplification of
      HIV-1 PND8

<400> SEQUENCE: 78
cctctgtgta acaaatgctc tccctggtcc                                    30

<210> SEQ ID NO 79
<211> LENGTH: 27
<212> TYPE: DNA
<213> ORGANISM: Artificial Sequence
<220> FEATURE:
<223> OTHER INFORMATION: sense primer(SstII-PND) for PCR amplification
      of HIV-1 PND8

<400> SEQUENCE: 79
aggcctccgc ggcagagggg accaggg                                       27

<210> SEQ ID NO 80
<211> LENGTH: 30
<212> TYPE: DNA
<213> ORGANISM: Artificial Sequence
<220> FEATURE:
<223> OTHER INFORMATION: antisense primer(PND-EagI) for PCR
      amplification of HIV-1 PND8

<400> SEQUENCE: 80
aacgttcggc cgtgtaacaa atgctctccc                                    30

<210> SEQ ID NO 81
<211> LENGTH: 77
<212> TYPE: DNA
<213> ORGANISM: Artificial Sequence
<220> FEATURE:
<223> OTHER INFORMATION: primer 1/Sst II for ligation-free PCR
      amplification of PVm-150 and PVm-150/M

<400> SEQUENCE: 81
attataccgc gggctaaggc cgttgcagcc tggaccctga agccgctgc aggccaagcc    60 tccaccgaag gcgactg                                                  77

<210> SEQ ID NO 82
<211> LENGTH: 70
<212> TYPE: DNA
<213> ORGANISM: Artificial Sequence
<220> FEATURE:
<223> OTHER INFORMATION: primer 2 for ligation-free PCR amplification
      of PVm-150

<400> SEQUENCE: 82
gctggctcgc ttggtagggg catcgttatc gacctcgatg atggctgggc aaccgcagtc   60

```
<210> SEQ ID NO 83
<211> LENGTH: 70
<212> TYPE: DNA
<213> ORGANISM: Artificial Sequence
<220> FEATURE:
<223> OTHER INFORMATION: primer 3 for ligation-free PCR of PVm-150

<400> SEQUENCE: 83
accaagcgag ccagcaagct cttcagcgaa ttcgaggtcg ataatgagca gcccactacc      60
cgagcccaga                                                            70

<210> SEQ ID NO 84
<211> LENGTH: 70
<212> TYPE: DNA
<213> ORGANISM: Artificial Sequence
<220> FEATURE:
<223> OTHER INFORMATION: primer 4 for ligation-free PCR amplification
      of PVm-150

<400> SEQUENCE: 84
cgcttagttg gcgcatcatt gtccttgtaa gtgatacgcc acatggcgaa gagcttctgg      60
gctcgggtag                                                            70

<210> SEQ ID NO 85
<211> LENGTH: 70
<212> TYPE: DNA
<213> ORGANISM: Artificial Sequence
<220> FEATURE:
<223> OTHER INFORMATION: primer 5 for ligation-free PCR amplification of
      PVm-150

<400> SEQUENCE: 85
tgcgccaact aagcgcgcat ctaaactgtg cgtccgaatc tacatgaagc ccaagcacgt      60
tcgatgctcc                                                            70

<210> SEQ ID NO 86
<211> LENGTH: 70
<212> TYPE: DNA
<213> ORGANISM: Artificial Sequence
<220> FEATURE:
<223> OTHER INFORMATION: primer 6 for ligation-free PCR amplification
      of PVm-150

<400> SEQUENCE: 86
ttgatgcccg tttggttggt gcgtcgttat ccacttcgat aatagcggga cagccggagc      60
atcgaacgtg                                                            70

<210> SEQ ID NO 87
<211> LENGTH: 70
<212> TYPE: DNA
<213> ORGANISM: Artificial Sequence
<220> FEATURE:
<223> OTHER INFORMATION: primer 7 for ligation-free PCR amplification of
      PVm-150

<400> SEQUENCE: 87
ccaaacgggc atcaaagctg acaactacc agtccccatg cgcgatcaac gagcaaccta      60
ccacccgtgc                                                            70

<210> SEQ ID NO 88
<211> LENGTH: 82
```

<210> SEQ ID NO 89
<211> LENGTH: 70
<212> TYPE: DNA
<213> ORGANISM: Artificial Sequence
<220> FEATURE:
<223> OTHER INFORMATION: primer 8/Eag I for ligation-free PCR amplification of PVm-150

<400> SEQUENCE: 88
tattaacggc cgacaacctg agggaaccac gacgcgggtc tgatagaagc acccagcgga    60
cttttgcgca c

-continued

```
        PVm-150/M

<400> SEQUENCE: 93
tactggcacg ctttgttgga gcatcgttat ccacttcaat aatggcggga cagccggagc      60
atcgaacgtg                                                             70

<210> SEQ ID NO 94
<211> LENGTH: 70
<212> TYPE: DNA
<213> ORGANISM: Artificial Sequence
<220> FEATURE:
<223> OTHER INFORMATION: primer 7 for ligation-free PCR amplification of
      PVm-150/M

<400> SEQUENCE: 94
caaagcgtgc cagtaaatta gacaactacc agtccccatg cgcgatcaat gaacaaccaa      60
ccacccgggc                                                             70

<210> SEQ ID NO 95
<211> LENGTH: 82
<212> TYPE: DNA
<213> ORGANISM: Artificial Sequence
<220> FEATURE:
<223> OTHER INFORMATION: primer 8/Eag I for ligation-free PCR
      amplification of PVm-150/M

<400> SEQUENCE: 95
tattaacggc cgacaacctg agggaaccac gacgcgggtc tgatagaagc acccagcgga      60
tttctgtgcc cgggtggttg gt                                               82
```

What is claimed is:

1. A method for improving a genetic stability of a foreign insert nucleotide sequence in a recombinant poliovirus vector, which comprises performing a mutagenesis of the foreign insert nucleotide sequence (a) to provide oven distribution of G/C content throughout the overall foreign insert nucleotide sequence and/or (b) to increase G/C content of the foreign insert without substantially causing amino acid substitutions.

2. The method according to claim 1, wherein the mutagenesis renders the foreign insert nucleotide sequence to have the G/C content of more than 30%.

3. The method according to claim 2 wherein the mutagenesis renders the foreign insert nucleotide sequence to have the G/C content of more than 40%.

4. The method according to claim 1, wherein the mutagenesis of the insert nucleotide sequence to provide even distribution of G/C content is performed by increasing G/C content of local A/T-rich region in the foreign insert nucleotide sequence.

5. The method according to claim 4, wherein the mutagenesis renders the local A/T-rich region of the foreign insert nucleotide sequence to have the G/C content of more than 30%.

6. The method according to claim 5, wherein the mutagenesis renders the local A/T-rich region of the foreign insert nucleotide sequence to have the G/C content of more than 40%.

7. The method according to any one of claims 1, 2, 3, 4, 5 and 6, wherein the mutagenesis is performed by silent mutations.

8. The method according to any one of claims 1, 2, 3, 4, 5 and 6, wherein the foreign insert nucleotide sequence is smaller than 450 bp in size.

9. The method according to claim 8, wherein the foreign insert nucleotide sequence is smaller than 450 bp in size.

10. The method according to claim 1, wherein the poliovirus is one selected from the group consisting of poliovirus type 1, poliovirus type 2 and poliovirus type 3.

11. The method according to claim 1, wherein the poliovirus is one selected from the group consisting of poliovirus Sabin type 1, poliovirus Sabin type 2 and poliovirus Sabin type 3.

12. The method according to claim 11 wherein the poliovirus is poliovirus Sabin type 1.

13. The method according to claim 1, wherein the foreign insert nucleotide sequence encodes a polypeptide antigen selected from the group consisting of bacterial polypeptide antigens, viral polypeptide antigens, fungal polypeptide antigens and eukaryotic parasite polypeptide antigens.

14. The method according to claim 13, wherein the foreign insert nucleotide sequence encodes a polypeptide antigen of an infectious virus selected from human immunodeficiency virus, simian immunodeficiency virus, hepatitis A virus, hepatitis B virus, hepatitis C virus, poliovirus, human papilloma virus, herpes simplex virus, rotavirus, influenza virus and epidemic hemorrhagic fever virus.

15. The method according to claim 14, wherein the polypeptide or a protein antigen is derived from the coding region covering the antigenic determinant sites.

16. The method according to claim 13 or 14, wherein the foreign insert nucleotide sequence encoding the polypeptide antigen is dimeric or multimeric.

17. The method according to claim 16, wherein the dimeric or multimeric foreign insert is homo/hetero-dimer or homo/hetero-multimer.

18. A method for constructing a recombinant poliovirus containing a foreign insert nucleotide sequence, which comprises the steps of:
  (a) performing a mutagenesis of the foreign insert nucleotide sequence (i) to provide even distribution of G/C content throughout the overall foreign insert nucleotide sequence and/or (ii) to increase G/C content of the foreign insert without substantially causing amino acid substitutions; and
  (b) introducing the foreign insert into a viral genome of a parent RNA virus to construct the recombinant poliovirus,
  wherein the foreign insert nucleotide sequence is introduced in such a manner that recombinant poliovirus is not disrupted for viral propagation.

19. The method according to claim 18, wherein the foreign insert nucleotide sequence has the G/C content of more than 40%.

20. The method according to claim 18, wherein the mutagenesis of the foreign insert nucleotide sequence to provide even distribution of G/C content is performed by increasing G/C content of local A/T-rich region of the foreign insert nucleotide sequence.

21. The method according to claim 20, wherein the mutagenesis at a local A/T-rich region renders the region to have the G/C content of more than 30%.

22. The method according to claim 21, wherein the mutagenesis at a local A/T-rich region renders the region to have the G/C content of more than 40%.

23. The method according to claim 18, wherein the mutagenesis performed by silent mutations.

24. The method according to any one of claims 19, 20, 21, 22 and 23, wherein the insert nucleotide sequence is smaller than 480 bp in size.

25. The method according to claim 24, wherein the foreign insert nucleotide sequence is smaller than 450 bp in size.

26. The method according to claim 18, wherein the poliovirus is one selected from the group consisting of poliovirus type 1, poliovirus type 2 and poliovirus type 3.

27. The method according to claim 18, wherein the poliovirus is one selected from the group consisting of poliovirus Sabin type 1, poliovirus Sabin type 2 and poliovirus Sabin type 3.

28. The method according to claim 27, wherein the poliovirus is poliovirus Sabin type 1.

29. The method according to claim 18, wherein the foreign insert nucleotide sequence encodes a polypeptide antigen selected from the group consisting of bacterial polypeptide antigens, viral polypeptide antigens, fungal polypeptide antigens and eukaryotic parasite polypeptide antigens.

30. The method according to claim 29, wherein the foreign insert nucleotide sequence encodes a polypeptide antigen of an infectious virus selected from human immunodeficiency virus, simian immunodeficiency virus, hepatitis A virus, hepatitis B virus, hepatitis C virus, poliovirus, human papilloma virus, herpes simplex virus, rotavirus, influenza virus and epidemic hemorrhagic fever virus.

31. The method according to claim 30, wherein the polypeptide or a protein antigen is derived from the coding region covering the major or minor antigenic determinant sites.

32. The method according to claims 30 or 31, wherein the foreign insert nucleotide sequence encoding the polypeptide antigen is dimeric or multimeric.

33. The method according to claim 32, wherein the dimeric or multimeric foreign insert is homo/hetero-dimer or homo/hetero-multimeric.

34. A recombinant poliovirus comprising a foreign insert nucleotide sequence, characterized in that the recombinant poliovirus is constituted by the method according to any one of claims 18, 19, 20, 21, 22, 23.

35. The recombinant poliovirus according to claim 34, wherein the foreign insert nucleotide sequence is smaller than 480 bp in size.

36. The recombinant poliovirus according to claim 35, wherein the foreign insert nucleotide sequence is smaller than 450 bp in size.

37. The recombinant poliovirus according to claim 34, wherein the poliovirus is one selected from the group consisting of poliovirus type 1, poliovirus type 2 and poliovirus type 3.

38. The recombinant poliovirus according to claim 37, wherein the poliovirus is one selected from the group consisting of poliovirus Sabin type 1, poliovirus Sabin type 2 and poliovirus Sabin type 3.

39. The recombinant poliovirus according to claim 38, wherein the poliovirus is poliovirus Sabin type 1.

40. The recombinant poliovirus according to claim 34, wherein the foreign insert nucleotide sequence encodes a polypeptide antigen selected from the group consisting of bacterial polypeptide antigens, viral polypeptide antigens, fungal polypeptide antigens and eukaryotic parasite polypeptide antigens.

41. The recombinant poliovirus according to claim 40, wherein the foreign insert nucleotide sequence encodes a polypeptide antigen of an infectious virus selected from human immunodeficiency virus, simian immunodeficiency virus, hepatitis A virus, hepatitis B virus, hepatitis C virus, poliovirus, human papilloma virus, herpes simplex virus, rotavirus, influenza virus and epidemic hemorrhagic fever virus.

42. The recombinant poliovirus according to claim 41, wherein the polypeptide or the protein antigen is derived from the coding region covering the major or minor antigenic determinant sites.

43. The recombinant poliovirus according to claims 41 or 42, wherein the foreign insert nucleotide sequence encoding the polypeptide antigen is dimeric or multimeric.

44. The recombinant poliovirus according to claim 43, wherein the dimeric or multimeric foreign insert is homo/hetero-dimer or homo/hetero-multimer.

45. The recombinant poliovirus according to claim 34, wherein recombinant poliovirus comprises:
  (a) a genomic nucleotide sequence of a parent poliovirus;
  (b) an additional polioviral cleavage site; and
  (c) the foreign insert nucleotide sequence,
  wherein the foreign insert nucleotide sequence is introduced into the viral genome of a parent poliovirus without disrupting the viral infection and proliferation, and a poliovirus protease also acts on the additional cleavage site so that the polypeptide or protein antigen encoded by the foreign insert nucleotide sequence is released from a polyprotein precursor of the recombinant poliovirus.

* * * * *